US006297028B1

(12) United States Patent
Taniguchi et al.

(10) Patent No.: US 6,297,028 B1
(45) Date of Patent: Oct. 2, 2001

(54) IL-2R-ASSOCIATED POLYPEPTIDE AND DNA MOLECULES CODING THEREFOR

(75) Inventors: Tadatsugu Taniguchi, Ibaraki; Hiroshi Shibuya, Aichi; Edward Leon Barsoumian, Osaka, all of (JP)

(73) Assignee: Boehringer Ingelheim International GmbH, Ingelheim (DE)

( * ) Notice: Subject to any disclaimer, the term of this patent is extended or adjusted under 35 U.S.C. 154(b) by 0 days.

(21) Appl. No.: 08/860,656

(22) PCT Filed: Dec. 23, 1995

(86) PCT No.: PCT/EP95/05123

§ 371 Date: Jan. 15, 1998

§ 102(e) Date: Jan. 15, 1998

(87) PCT Pub. No.: WO96/21732

PCT Pub. Date: Jul. 18, 1996

(30) Foreign Application Priority Data

Jan. 9, 1995 (EP) .......... 95100201

(51) Int. Cl.$^7$ .......... C12P 21/06; C07K 1/00; C07H 21/04

(52) U.S. Cl. .......... 435/69.1; 435/252.3; 435/320.1; 530/350; 536/23.5; 536/24.3; 514/2; 514/8

(58) Field of Search .......... 536/23.5, 24.3; 435/69.1, 252.3, 320.1; 530/350; 514/2, 8

(56) References Cited

U.S. PATENT DOCUMENTS 5,198,359 * 3/1993 Taniguchi et al. .......... 435/252.3
5,352,772 * 10/1994 Smith et al. .......... 530/350
5,356,795 * 10/1994 Leonard .......... 435/69.1
5,510,259 * 4/1996 Sugumura et al. .......... 435/240.2
5,837,816 * 11/1998 Ciardelli et al. .......... 530/350
5,856,140 * 1/1999 Shimamura et al. .......... 435/69.1

FOREIGN PATENT DOCUMENTS 0 621 338 10/1994 (EP) .

OTHER PUBLICATIONS

Adams et al., Acc. No. AA312336, 1995.*
Adams et al., Acc. No. AA357861, 1997 Rao et al., Acc. No. P11415, 1989.*
Matsubara et al., Acc. No. T26803, 1996 Gonzalez et al., Acc. No. PN0448, 1993.*
Randoranoki et al., Acc. No. JS0230, 1990.*
Babigechuk et al., Acc. No., S57614.*
Wood et al., Acc. No. 042909, 1998.*
Doi, T. et al., "Human interleukin 2 (IL 2) receptor β chain allows transduction of IL 2–induced proliferation signal(s) in a murine cell line," *Eur. J. Immunol.* 19:2375–2378 (1989).
Durfee, T. et al., "The retinoblastoma protein associates with the protein phosphatase type 1 catalytic subunit," *Gene Dev.* 7:555–569 (1993).
Fields, S. and Song, O., "A novel genetic system to detect protein–protein interactions," *Nature* 340:245–246 (1989).
Greene, W.C. and Leonard, W.J., "The Human Interleukin–2 Receptor," *Annu. Rev. Immunol.* 4:69–95 (1986).
Hatakeyama, M. et al., "A Restricted Cytoplasmic Region of IL–2 Receptor β Chain is Essential for Growth Signal Transduction but Not for Ligand Binding and Internalization," *Cell* 59:837–845 (1989).
Hatakeyama, M. et al., "Interleukin–2 Receptor β Chain Gene: Generation of Three Receptor Forms by Cloned Human α and β Chain cDNA's," *Science* 244:551–556 (1989).
Hatakeyama, M. et al., "Interaction of the IL–2 Receptor with the src–Family Kinase P56$^{lck}$ :Identification of Novel Intermolecular Association," *Science* 252:1523–1528 (1991).
Hatakeyama, M. et al., "*c–fos* gene induction by interleukin 2: Identification of the critical cytoplasmic regions within the interleukin 2 receptor β chain," *Proc. Natl. Acad. Sci. USA* 89:2022–2026 (1992).
Johnston, J.A. et al., "Phosphorylation and activation of the Jak–3 Janus kinase in response to interleukin–2," *Nature* 370:151–153 (Jul. 1994).
Kawahara, A. et al., "Evidence for a critical Role for the Cytoplasmic Region of the Interleukin 2 (IL–2) Receptor γ Chain in IL–2, IL–4, and IL–7 Signalling," *Mol. Cell. Biol.* 14:5433–5440 (Aug. 1994).
Kobayashi, N. et al., "Functional coupling of the src–family protein tyrosine kinases p59$^{fyn}$ and p53/56$^{lyn}$ with the interleukin 2 receptor: Implications for redundancy and pleiotropism in cytokine signal transduction," *Proc. Natl. Acad. Sci. USA* 90:4201–4205 (1993).
Kondo, M. et al., "Functional Participation of the IL–2 Receptor Y Chain in IL–7 Receptor Complexes," *Science* 263:1453–1454 (Mar. 1994).
Kondo, M. et al., "Sharing of the Interleukin–2 (IL–2) Receptor γ Chain Between Receptors for IL–2 and IL–4," *Science 262*:1874–1877 (1993).
Kono, T. et al., "Murine interleukin 2 receptor βchain: Dysregulated gene expression in lymphoma line EL–4 caused by a promoter insertion," *Proc. Natl. Acad. Sci. USA 87*:1806–1810 (1990).
Minami, Y. et al., "The IL–2 Receptor Complex: Its Structure, Function, and Target Genes," *Annu. Rev. Immunol. 11*:245–267 (1993).

(List continued on next page.)

*Primary Examiner*—Gary L. Kunz
*Assistant Examiner*—Michael Brannock
(74) *Attorney, Agent, or Firm*—Sterne, Kessler, Goldstein & Fox P.L.L.C.

(57) ABSTRACT

The present invention relates to a polypeptide, p43, which is associated with the interleukin-2 receptor (IL-2R). It binds specifically to the β and γ subunits of IL-2R and is further capable of binding NAD$^+$. The invention is further related to nucleic acid molecules coding for p43 and to antibodies specifically binding to p43.

12 Claims, 9 Drawing Sheets

OTHER PUBLICATIONS

Minami, Y. et al., "Association of p56$^{lck}$ with IL–2 receptor β chain is critical for the IL–2–induced activation of p56$^{lck}$," *EMBO J. 12*:759–768 (1993).

Minami, Y. et al., "Protein Tyrosine Kinase Syk Is Associated with and Activated by the IL–2 Receptor: Possible Link with the c–myc Induction Pathway," *Immunity 2*: 89–100 (Jan. 1995).

Nakamura, Y. et al., "Heterodimerization of the IL–2 receptor β– and γ–chain cytoplasmic domains is required for signalling," *Nature 369*:330–333 (May 1994).

Russell, S.M. et al., "Interleukin–2 Receptor γ Chain: A Functional Component of the Interleukin–4 Receptor," *Science 262*:1880–1883 (1993).

Satoh, T. et al., "Interleukin 2–induced Activation of Ras Requires Two Domains of Interleukin 2 Receptor β Subunit, the Essential Region for Growth Stimulation and Lck–binding Domain," *J. Biol. Chem. 267*:25423–25427 (1992).

Shibuya, H. et al., "New human gene encoding a positive modulator of HIV Tat–mediated transactivation," *Nature 357*:700–702 (1992).

Shibuya, H. et al., "IL–2 and EGF Receptors Stimulate the Hematopoietic Cell Cycle via Different Signaling Pathways: Demonstration of a Novel Role for c–myc," *Cell 70*:57–67 (1992).

Takeshita, T. et al., "Cloning of the γChain of the Human IL–2 Receptor," *Science 257*:379–382 (1992).

Witthuhn, B.A. et al., "Involvement of the Jak–3 Janus kinase in signalling by interleukins 2 and 4 in lymphoid and myeloid cells," *Nature 370*:153–157 (Jul. 1994).

Wunderlich, D. et al., "Use of recombinant fusion proteins for generation and rapid characterization of monoclonal antibodies: Application to the Kunitz domain of human β amyloid precursor protein," *J. Immunol. Meth. 147*:1–11 (1992).

Nelson, B.H. et al., "Cytoplasmic domains of the interleukin–2 receptor β and γ chains mediate the signal for T–cell proliferation," *Nature 369*:333–336 (May 1994).

Noguchi, M. et al., "Interleukin–2 Receptor γ Chain: A Functional Component of the Interleukin–7 Receptor," *Science 262*:1877–1880 (1993).

Noguchi, M. et al., "Interleukin–2 Receptor γ Chain Mutation Results in X–Linked Severe Combined Immunodeficiency in Humans," *Cell 73*:147–157 (1993).

* cited by examiner

```
     AGAATGGACAGAATACTGACTGGAACGTTAATTCGAGCATTTCATATGCGAAGAGCGGAATAACAGTTCCGTATTCTTC
     TTTCAGTTTCTCCATTAGATTAGCTTCATTTTCGAAGGCTCCGTTTTGCATGCTTAATTTTGAAACTAGCCCGTGGTTT
     GGCAGAATTTGACTGAATTCAGGGGTGAGAGTTTGATCCAGTCCAAGTGTATTTGAATTTGAGCACGCAGTTCAACCAG
     TGTTTACA
                 M   E   F   L   K   T   C   V   L   R   R   N   A   C   T   A   V    17
246              ATG GAA TTT CTG AAG ACT TGT GTA CTT AGA AGA AAT GCA TGC ACT GCG GTT

     C   F   W   R   S   K   V   V   Q   K   P   S   V   R   R   I   S   T   T   S    37
297  TGC TTC TGG AGA AGC AAA GTT GTC CAA AAG CCT TCA GTT AGA AGG ATT AGT ACT ACC TCT

     P   R   S   T   V   M   P   A   W   V   I   D   K   Y   G   K   N   E   V   L    57
357  CCA AGG AGC ACT GTC ATG CCT GCT TGG GTG ATA GAT AAA TAT GGG AAG AAT GAA GTG CTT

     R   F   T   Q   N   M   M   M   P   I   I   H   Y   P   N   E   V   I   V   K    77
417  CGA TTC ACT CAG AAC ATG ATG ATG CCT ATT ATA CAC TAT CCA AAT GAA GTC ATT GTC AAA

     V   H   A   A   S   V   N   P   I   D   V   N   M   R   S   G   Y   G   A   T    97
477  GTT CAC GCT GCC AGT GTA AAT CCT ATA GAC GTT AAT ATG AGA AGT GGT TAT GGA GCT ACA

     A   L   N   M   K   R   D   P   L   H   V   K   I   K   G   E   E   F   P   L    117
537  GCT TTA AAT ATG AAG CGT GAT CCT TTA CAC GTG AAA ATC AAA GGA GAA GAA TTT CCT CTG

     T   L   G   R   D   V   S   G   V   V   M   E   C   G   L   D   V   K   Y   F    137
597  ACT CTG GGT CGG GAT GTC TCT GGC GTG GTG ATG GAA TGT GGG CTT GAT GTG AAA TAC TTC

     K   P   G   D   E   V   W   A   A   V   P   P   W   K   Q   G   T   L   S   E    157
657  AAG CCT GGA GAT GAG GTC TGG GCT GCA GTT CCT CCT TGG AAA CAA GGC ACT CTT TCA GAG

     F   V   V   V   S   G   N   E   V   S   H   K   P   K   S   L   T   H   T   Q    177
717  TTT GTT GTA GTC AGT GGG AAT GAG GTC TCT CAC AAA CCC AAA TCA CTC ACT CAT ACT CAA

     A   A   S   L   P   Y   V   A   L   T   A   W   S   A   I   N   K   V   G   G    197
777  GCT GCC TCT TTG CCA TAT GTG GCT CTC ACA GCC TGG TCT GCT ATA AAC AAA GTT GGT GGC
```

FIG. 1A

```
      L   N   D   K   N   C   T   G   K   R   V   L   I   L   G   A   S   G   G   V    217
837   CTG AAT GAC AAG AAT TGC ACA GGA AAA CGT GTT CTA ATC TTA GGC GCT TCA GGC GGA GTT

      G   T   F   A   I   Q   V   M   K   A   W   D   A   H   V   T   A   V   C   S    237
897   GGT ACT TTT GCT ATA CAG GTA ATG AAA GCA TGG GAT GCT CAT GTG ACA GCA GTT TGC TCC

      Q   D   A   S   E   L   V   R   K   L   G   A   D   D   V   I   D   Y   K   S    257
957   CAA GAT GCC AGT GAA CTT GTA AGG AAG CTT GGT GCA GAC GAT GTA ATT GAT TAC AAA TCT

      G   S   V   E   E   Q   L   K   S   L   K   P   F   D   F   I   L   D   N   V    277
1017  GGA AGT GTG GAA GAG CAG TTG AAA TCC TTA AAA CCA TTT GAT TTT ATC CTT GAT AAT GTT

      G   G   S   T   E   T   W   A   P   D   F   L   K   K   W   S   G   A   T   Y    297
1077  GGC GGA TCC ACT GAA ACA TGG GCT CCA GAT TTT CTC AAG AAA TGG TCA GGA GCC ACC TAT

      V   T   L   V   T   P   F   L   L   N   M   D   R   L   G   I   A   D   G   M    317
1137  GTG ACT TTG GTG ACT CCT TTC CTC CTG AAC ATG GAC CGA TTG GGC ATA GCA GAT GGC ATG

      L   Q   T   G   V   T   V   G   S   K   A   L   K   H   F   W   K   G   V   H    337
1197  TTG CAG ACA GGA GTC ACT GTA GGT TCA AAG GCA TTA AAG CAT TTC TGG AAA GGA GTC CAT

      Y   R   W   A   F   F   M   A   S   G   P   C   L   D   D   I   A   E   L   V    357
1257  TAT CGC TGG GCA TTT TTC ATG GCC AGT GGC CCA TGT TTA GAT GAC ATT GCA GAA CTG GTG

      D   A   G   K   I   R   P   V   I   E   Q   T   F   P   F   S   K   V   P   E    377
1317  GAT GCG GGA AAG ATC CGG CCA GTT ATT GAA CAA ACC TTT CCT TTT TCT AAA GTT CCA GAA

      A   F   L   K   V   E   R   G   H   A   R   G   K   T   V   I   N   V   V        396
1377  GCC TTC CTG AAG GTG GAA AGA GGA CAC GCA CGA GGA AAG ACT GTA ATT AAT GTT GTT TAA

1437  ATAAAAATGCAGTTTAGTGATTAAAAAAAAAAAAAAAAAAAAAA
```

FIG.1B

```
HUMAN p43 MEFLKTCVLR RNACTAVCFW RSKVVQKPSV RRISTTSPRS TVMPAWVIDK YGKNEVLRFT   60
          |??||||||| |?||?|?||| |??|??||?? |?|||||?|| |||||||||| ||||||||||
MOUSE p43 MGVLKTCVLR RSACAAACFW RRTVIPKPPF RGISTTSARS TVMPAWVIDK YGKNEVLRFT   60

HUMAN p43 QNMMMPIIHY PNEVIVKVHA ASVNPIDVNM RSGYGATALN MKRDPLHVKI KGEEFPLTLG  120
          ||||?||||| |||||?|||| |||||||||| |||||||||| |||||||?|? ||||||||||
MOUSE p43 QNMMLPIIHY PNEVIIKVHA ASVNPIDVNM RSGYGATALN MKRDPLHMKT KGEEFPLTLG  120

HUMAN p43 RDVSGVVMEC GLDVKYFKPG DEVWAAVPPW KQGTLSEFVV VSGNEVSHKP KSLTHTQAAS  180
          |||||||||| |||||||?|| |||||||||| |||||||||| |||||||||| ||||||||||
MOUSE p43 RDVSGVVMEC GLDVKYFQPG DEVWAAVPPW KQGTLSEFVV VSGNEVSHKP KSLTHTQAAS  180

HUMAN p43 LPYVALTAWS AINKVGGLND KNCTGKRVLI LGASGGVGTF AIQVMKAWDA HVTAVCSQDA  240
          |||||||||| ||||||||?| ?||?|||?|| |||||||||| ||||||||?| |||||||?||
MOUSE p43 LPYVALTAWS AINKVGGLSD RNCKGKRALI LGASGGVGTF AIQVMKAWGA HVTAVCSKDA  240

HUMAN p43 SELVRKLGAD DVIDYKSGSV EEQLKSLKPF DFILDNVGGS TETWAPDFLK KWSGATYVTL  300
          |||||||||| ?||||??||| ||||||||?? ?||||||||| |||||??||| ||||||||||
MOUSE p43 SELVRKLGAD EVIDYTLGSV EEQLKSLKLC AFILDNVGGS TETWALNFLK KWSGATYVTL  300

HUMAN p43 VTPFLLNMDR LGIADGMLQT GVTVGSKALK HFWKGVHYRW AFFMASGPCL DDIAELVDAG  360
          |||||||||| ||?||||||| |||||?||?| |?|?|||||| ||||||||?| |?||||||||
MOUSE p43 VTPFLLNMDR LGVADGMLQT GVTVGTKAMK HLWQGVHYRW AFFMASGPYL DEIAELVDAG  360

HUMAN p43 KIRPVIEQTF PFSKVPEAFL KVERGHARGK TVINVV                             396
          |||||||?|| |||?|||||| |||||||||| ||?|||
MOUSE p43 KIRPVIERTF PFSEVPEAFL KVERGHARGK TVVNVV                             396
```

FIG. 1C

SEQUENCE LISTING

```
<160> NUMBER OF SEQ ID NOS:   18

<210> SEQ ID NO 1
<211> LENGTH: 1481
<212> TYPE: DNA
<213> ORGANISM: Human p43
<220> FEATURE:
<221> NAME/KEY: CDS
<222> LOCATION: (246)..(1433)

<400> SEQUENCE: 1

agaatggaca gaatactgac tggaacgtta attcgagcat ttcatatgcg aagagcggaa      60

taacagttcc gtattcttct ttcagtttct ccattagatt agcttcattt tcgaaggctc     120

cgttttgcat gcttaatttt gaaactagcc cgtggtttgg cagaatttga ctgaattcag     180

gggtgagagt ttgatccagt ccaagtgtat ttgaatttga gcacgcagtt caaccagtgt     240

ttaca atg gaa ttt ctg aag act tgt gta ctt aga aga aat gca tgc act     290
      Met Glu Phe Leu Lys Thr Cys Val Leu Arg Arg Asn Ala Cys Thr
      1               5                   10                  15

gcg gtt tgc ttc tgg aga agc aaa gtt gtc caa aag cct tca gtt aga     338
Ala Val Cys Phe Trp Arg Ser Lys Val Val Gln Lys Pro Ser Val Arg
                20                  25                  30

agg att agt act acc tct cca agg agc act gtc atg cct gct tgg gtg     386
Arg Ile Ser Thr Thr Ser Pro Arg Ser Thr Val Met Pro Ala Trp Val
            35                  40                  45

ata gat aaa tat ggg aag aat gaa gtg ctt cga ttc act cag aac atg     434
Ile Asp Lys Tyr Gly Lys Asn Glu Val Leu Arg Phe Thr Gln Asn Met
        50                  55                  60

atg atg cct att ata cac tat cca aat gaa gtc att gtc aaa gtt cac     482
Met Met Pro Ile Ile His Tyr Pro Asn Glu Val Ile Val Lys Val His
    65                  70                  75

gct gcc agt gta aat cct ata gac gtt aat atg aga agt ggt tat gga     530
Ala Ala Ser Val Asn Pro Ile Asp Val Asn Met Arg Ser Gly Tyr Gly
```

-continued

```
80                  85                  90                  95

gct aca gct tta aat atg aag cgt gat cct tta cac gtg aaa atc aaa      578
Ala Thr Ala Leu Asn Met Lys Arg Asp Pro Leu His Val Lys Ile Lys
                100                 105                 110

gga gaa gaa ttt cct ctg act ctg ggt cgg gat gtc tct ggc gtg gtg      626
Gly Glu Glu Phe Pro Leu Thr Leu Gly Arg Asp Val Ser Gly Val Val
            115                 120                 125

atg gaa tgt ggg ctt gat gtg aaa tac ttc aag cct gga gat gag gtc      674
Met Glu Cys Gly Leu Asp Val Lys Tyr Phe Lys Pro Gly Asp Glu Val
        130                 135                 140

tgg gct gca gtt cct cct tgg aaa caa ggc act ctt tca gag ttt gtt      722
Trp Ala Ala Val Pro Pro Trp Lys Gln Gly Thr Leu Ser Glu Phe Val
    145                 150                 155

gta gtc agt ggg aat gag gtc tct cac aaa ccc aaa tca ctc act cat      770
Val Val Ser Gly Asn Glu Val Ser His Lys Pro Lys Ser Leu Thr His
160                 165                 170                 175

act caa gct gcc tct ttg cca tat gtg gct ctc aca gcc tgg tct gct      818
Thr Gln Ala Ala Ser Leu Pro Tyr Val Ala Leu Thr Ala Trp Ser Ala
                180                 185                 190

ata aac aaa gtt ggt ggc ctg aat gac aag aat tgc aca gga aaa cgt      866
Ile Asn Lys Val Gly Gly Leu Asn Asp Lys Asn Cys Thr Gly Lys Arg
            195                 200                 205

gtt cta atc tta ggc gct tca ggc gga gtt ggt act ttt gct ata cag      914
Val Leu Ile Leu Gly Ala Ser Gly Gly Val Gly Thr Phe Ala Ile Gln
        210                 215                 220

gta atg aaa gca tgg gat gct cat gtg aca gca gtt tgc tcc caa gat      962
Val Met Lys Ala Trp Asp Ala His Val Thr Ala Val Cys Ser Gln Asp
    225                 230                 235

gcc agt gaa ctt gta agg aag ctt ggt gca gac gat gta att gat tac     1010
Ala Ser Glu Leu Val Arg Lys Leu Gly Ala Asp Asp Val Ile Asp Tyr
240                 245                 250                 255

aaa tct gga agt gtg gaa gag cag ttg aaa tcc tta aaa cca ttt gat     1058
Lys Ser Gly Ser Val Glu Glu Gln Leu Lys Ser Leu Lys Pro Phe Asp
                260                 265                 270

ttt atc ctt gat aat gtt ggc gga tcc act gaa aca tgg gct cca gat     1106
Phe Ile Leu Asp Asn Val Gly Gly Ser Thr Glu Thr Trp Ala Pro Asp
            275                 280                 285

ttt ctc aag aaa tgg tca gga gcc acc tat gtg act ttg gtg act cct     1154
Phe Leu Lys Lys Trp Ser Gly Ala Thr Tyr Val Thr Leu Val Thr Pro
        290                 295                 300

ttc ctc ctg aac atg gac cga ttg ggc ata gca gat ggc atg ttg cag     1202
Phe Leu Leu Asn Met Asp Arg Leu Gly Ile Ala Asp Gly Met Leu Gln
    305                 310                 315

aca gga gtc act gta ggt tca aag gca tta aag cat ttc tgg aaa gga     1250
Thr Gly Val Thr Val Gly Ser Lys Ala Leu Lys His Phe Trp Lys Gly
320                 325                 330                 335

gtc cat tat cgc tgg gca ttt ttc atg gcc agt ggc cca tgt tta gat     1298
Val His Tyr Arg Trp Ala Phe Phe Met Ala Ser Gly Pro Cys Leu Asp
                340                 345                 350

gac att gca gaa ctg gtg gat gcg gga aag atc cgg cca gtt att gaa     1346
Asp Ile Ala Glu Leu Val Asp Ala Gly Lys Ile Arg Pro Val Ile Glu
            355                 360                 365

caa acc ttt cct ttt tct aaa gtt cca gaa gcc ttc ctg aag gtg gaa     1394
Gln Thr Phe Pro Phe Ser Lys Val Pro Glu Ala Phe Leu Lys Val Glu
        370                 375                 380

aga gga cac gca cga gga aag act gta att aat gtt gtt taaataaaaa      1443
Arg Gly His Ala Arg Gly Lys Thr Val Ile Asn Val Val
    385                 390                 395

tgcagtttag tgattaaaaa aaaaaaaaaa aaaaaaa                            1481
```

-continued

<210> SEQ ID NO 2
<211> LENGTH: 396
<212> TYPE: PRT
<213> ORGANISM: Human p43

<400> SEQUENCE: 2

```
Met Glu Phe Leu Lys Thr Cys Val Leu Arg Arg Asn Ala Cys Thr Ala
1               5                   10                  15

Val Cys Phe Trp Arg Ser Lys Val Val Gln Lys Pro Ser Val Arg Arg
            20                  25                  30

Ile Ser Thr Thr Ser Pro Arg Ser Thr Val Met Pro Ala Trp Val Ile
        35                  40                  45

Asp Lys Tyr Gly Lys Asn Glu Val Leu Arg Phe Thr Gln Asn Met Met
    50                  55                  60

Met Pro Ile Ile His Tyr Pro Asn Glu Val Ile Val Lys Val His Ala
65                  70                  75                  80

Ala Ser Val Asn Pro Ile Asp Val Asn Met Arg Ser Gly Tyr Gly Ala
                85                  90                  95

Thr Ala Leu Asn Met Lys Arg Asp Pro Leu His Val Lys Ile Lys Gly
            100                 105                 110

Glu Glu Phe Pro Leu Thr Leu Gly Arg Asp Val Ser Gly Val Val Met
        115                 120                 125

Glu Cys Gly Leu Asp Val Lys Tyr Phe Lys Pro Gly Asp Glu Val Trp
    130                 135                 140

Ala Ala Val Pro Pro Trp Lys Gln Gly Thr Leu Ser Glu Phe Val Val
145                 150                 155                 160

Val Ser Gly Asn Glu Val Ser His Lys Pro Lys Ser Leu Thr His Thr
                165                 170                 175

Gln Ala Ala Ser Leu Pro Tyr Val Ala Leu Thr Ala Trp Ser Ala Ile
            180                 185                 190

Asn Lys Val Gly Gly Leu Asn Asp Lys Asn Cys Thr Gly Lys Arg Val
        195                 200                 205

Leu Ile Leu Gly Ala Ser Gly Gly Val Gly Thr Phe Ala Ile Gln Val
    210                 215                 220

Met Lys Ala Trp Asp Ala His Val Thr Ala Val Cys Ser Gln Asp Ala
225                 230                 235                 240

Ser Glu Leu Val Arg Lys Leu Gly Ala Asp Asp Val Ile Asp Tyr Lys
                245                 250                 255

Ser Gly Ser Val Glu Glu Gln Leu Lys Ser Leu Lys Pro Phe Asp Phe
            260                 265                 270

Ile Leu Asp Asn Val Gly Gly Ser Thr Glu Thr Trp Ala Pro Asp Phe
        275                 280                 285

Leu Lys Lys Trp Ser Gly Ala Thr Tyr Val Thr Leu Val Thr Pro Phe
    290                 295                 300

Leu Leu Asn Met Asp Arg Leu Gly Ile Ala Asp Gly Met Leu Gln Thr
305                 310                 315                 320

Gly Val Thr Val Gly Ser Lys Ala Leu Lys His Phe Trp Lys Gly Val
                325                 330                 335

His Tyr Arg Trp Ala Phe Phe Met Ala Ser Gly Pro Cys Leu Asp Asp
            340                 345                 350

Ile Ala Glu Leu Val Asp Ala Gly Lys Ile Arg Pro Val Ile Glu Gln
        355                 360                 365

Thr Phe Pro Phe Ser Lys Val Pro Glu Ala Phe Leu Lys Val Glu Arg
```

-continued

```
    370                 375                 380

Gly His Ala Arg Gly Lys Thr Val Ile Asn Val Val
385                 390                 395


<210> SEQ ID NO 3
<211> LENGTH: 396
<212> TYPE: PRT
<213> ORGANISM: Human p43

<400> SEQUENCE: 3

Met Glu Phe Leu Lys Thr Cys Val Leu Arg Arg Asn Ala Cys Thr Ala
1               5                   10                  15

Val Cys Phe Trp Arg Ser Lys Val Val Gln Lys Pro Ser Val Arg Arg
            20                  25                  30

Ile Ser Thr Thr Ser Pro Arg Ser Thr Val Met Pro Ala Trp Val Ile
        35                  40                  45

Asp Lys Tyr Gly Lys Asn Glu Val Leu Arg Phe Thr Gln Asn Met Met
    50                  55                  60

Met Pro Ile Ile His Tyr Pro Asn Glu Val Ile Val Lys Val His Ala
65                  70                  75                  80

Ala Ser Val Asn Pro Ile Asp Val Asn Met Arg Ser Gly Tyr Gly Ala
                85                  90                  95

Thr Ala Leu Asn Met Lys Arg Asp Pro Leu His Val Lys Ile Lys Gly
            100                 105                 110

Glu Glu Phe Pro Leu Thr Leu Gly Arg Asp Val Ser Gly Val Val Met
        115                 120                 125

Glu Cys Gly Leu Asp Val Lys Tyr Phe Lys Pro Gly Asp Glu Val Trp
    130                 135                 140

Ala Ala Val Pro Pro Trp Lys Gln Gly Thr Leu Ser Glu Phe Val Val
145                 150                 155                 160

Val Ser Gly Asn Glu Val Ser His Lys Pro Lys Ser Leu Thr His Thr
                165                 170                 175

Gln Ala Ala Ser Leu Pro Tyr Val Ala Leu Thr Ala Trp Ser Ala Ile
            180                 185                 190

Asn Lys Val Gly Gly Leu Asn Asp Lys Asn Cys Thr Gly Lys Arg Val
        195                 200                 205

Leu Ile Leu Gly Ala Ser Gly Gly Val Gly Thr Phe Ala Ile Gln Val
    210                 215                 220

Met Lys Ala Trp Asp Ala His Val Thr Ala Val Cys Ser Gln Asp Ala
225                 230                 235                 240

Ser Glu Leu Val Arg Lys Leu Gly Ala Asp Asp Val Ile Asp Tyr Lys
                245                 250                 255

Ser Gly Ser Val Glu Glu Gln Leu Lys Ser Leu Lys Pro Phe Asp Phe
            260                 265                 270

Ile Leu Asp Asn Val Gly Gly Ser Thr Glu Thr Trp Ala Pro Asp Phe
        275                 280                 285

Leu Lys Lys Trp Ser Gly Ala Thr Tyr Val Thr Leu Val Thr Pro Phe
    290                 295                 300

Leu Leu Asn Met Asp Arg Leu Gly Ile Ala Asp Gly Met Leu Gln Thr
305                 310                 315                 320

Gly Val Thr Val Gly Ser Lys Ala Leu Lys His Phe Trp Lys Gly Val
                325                 330                 335

His Tyr Arg Trp Ala Phe Phe Met Ala Ser Gly Pro Cys Leu Asp Asp
            340                 345                 350
```

-continued

```
Ile Ala Glu Leu Val Asp Ala Gly Lys Ile Arg Pro Val Ile Glu Gln
        355                 360                 365

Thr Phe Pro Phe Ser Lys Val Pro Glu Ala Phe Leu Lys Val Glu Arg
    370                 375                 380

Gly His Ala Arg Gly Lys Thr Val Ile Asn Val Val
385                 390                 395


<210> SEQ ID NO 4
<211> LENGTH: 396
<212> TYPE: PRT
<213> ORGANISM: Mouse p43

<400> SEQUENCE: 4

Met Gly Val Leu Lys Thr Cys Val Leu Arg Arg Ser Ala Cys Ala Ala
1               5                   10                  15

Ala Cys Phe Trp Arg Arg Thr Val Ile Pro Lys Pro Pro Phe Arg Gly
            20                  25                  30

Ile Ser Thr Thr Ser Ala Arg Ser Thr Val Met Pro Ala Trp Val Ile
        35                  40                  45

Asp Lys Tyr Gly Lys Asn Glu Val Leu Arg Phe Thr Gln Asn Met Met
    50                  55                  60

Leu Pro Ile Ile His Tyr Pro Asn Glu Val Ile Ile Lys Val His Ala
65                  70                  75                  80

Ala Ser Val Asn Pro Ile Asp Val Asn Met Arg Ser Gly Tyr Gly Ala
                85                  90                  95

Thr Ala Leu Asn Met Lys Arg Asp Pro Leu His Met Lys Thr Lys Gly
            100                 105                 110

Glu Glu Phe Pro Leu Thr Leu Gly Arg Asp Val Ser Gly Val Val Met
        115                 120                 125

Glu Cys Gly Leu Asp Val Lys Tyr Phe Gln Pro Gly Asp Glu Val Trp
    130                 135                 140

Ala Ala Val Pro Pro Trp Lys Gln Gly Thr Leu Ser Glu Phe Val Val
145                 150                 155                 160

Val Ser Gly Asn Glu Val Ser His Lys Pro Lys Ser Leu Thr His Thr
                165                 170                 175

Gln Ala Ala Ser Leu Pro Tyr Val Ala Leu Thr Ala Trp Ser Ala Ile
            180                 185                 190

Asn Lys Val Gly Gly Leu Ser Asp Arg Asn Cys Lys Gly Lys Arg Ala
        195                 200                 205

Leu Ile Leu Gly Ala Ser Gly Gly Val Gly Thr Phe Ala Ile Gln Val
    210                 215                 220

Met Lys Ala Trp Gly Ala His Val Thr Ala Val Cys Ser Lys Asp Ala
225                 230                 235                 240

Ser Glu Leu Val Arg Lys Leu Gly Ala Asp Glu Val Ile Asp Tyr Thr
                245                 250                 255

Leu Gly Ser Val Glu Glu Gln Leu Lys Ser Leu Lys Leu Cys Ala Phe
            260                 265                 270

Ile Leu Asp Asn Val Gly Gly Ser Thr Glu Thr Trp Ala Leu Asn Phe
        275                 280                 285

Leu Lys Lys Trp Ser Gly Ala Thr Tyr Val Thr Leu Val Thr Pro Phe
    290                 295                 300

Leu Leu Asn Met Asp Arg Leu Gly Val Ala Asp Gly Met Leu Gln Thr
305                 310                 315                 320

Gly Val Thr Val Gly Thr Lys Ala Met Lys His Leu Trp Gln Gly Val
                325                 330                 335
```

-continued

```
His Tyr Arg Trp Ala Phe Phe Met Ala Ser Gly Pro Tyr Leu Asp Glu
            340                 345                 350

Ile Ala Glu Leu Val Asp Ala Gly Lys Ile Arg Pro Val Ile Glu Arg
        355                 360                 365

Thr Phe Pro Phe Ser Glu Val Pro Glu Ala Phe Leu Lys Val Glu Arg
    370                 375                 380

Gly His Ala Arg Gly Lys Thr Val Val Asn Val Val
385                 390                 395


<210> SEQ ID NO 5
<211> LENGTH: 30
<212> TYPE: DNA
<213> ORGANISM: Oligonucleotide Primer

<400> SEQUENCE: 5

atttcccggg ggaacggacg atgccccgaa                                      30


<210> SEQ ID NO 6
<211> LENGTH: 30
<212> TYPE: DNA
<213> ORGANISM: Oligonucleotide Primer

<400> SEQUENCE: 6

cttctgtcga cggattgggg ttcaggtttc                                      30


<210> SEQ ID NO 7
<211> LENGTH: 20
<212> TYPE: DNA
<213> ORGANISM: Oligonucleotide Primer

<400> SEQUENCE: 7

caggatgggc gttttgaaga                                                 20


<210> SEQ ID NO 8
<211> LENGTH: 20
<212> TYPE: DNA
<213> ORGANISM: Oligonucleotide Primer

<400> SEQUENCE: 8

gtcttcaaaa cgcccatcct                                                 20


<210> SEQ ID NO 9
<211> LENGTH: 1188
<212> TYPE: DNA
<213> ORGANISM: Human p43 cDNA

<400> SEQUENCE: 9

atggaatttc tgaagacttg tgtacttaga agaaatgcat gcactgcggt ttgcttctgg     60

agaagcaaag ttgtccaaaa gccttcagtt agaaggatta gtactacctc tccaaggagc    120

actgtcatgc ctgcttgggt gatagataaa tatgggaaga atgaagtgct tcgattcact    180

cagaacatga tgatgcctat tatacactat ccaaatgaag tcattgtcaa agttcacgct    240

gccagtgtaa atcctataga cgttaatatg agaagtggtt atggagctac agctttaaat    300

atgaagcgtg atcctttaca cgtgaaaatc aaaggagaag aatttcctct gactctgggt    360

cgggatgtct ctggcgtggt gatggaatgt gggcttgatg tgaaatactt caagcctgga    420

gatgaggtct gggctgcagt tcctccttgg aaacaaggca ctctttcaga gtttgttgta    480

gtcagtggga atgaggtctc tcacaaaccc aaatcactca ctcatactca agctgcctct    540
```

-continued

```
ttgccatatg tggctctcac agcctggtct gctataaaca aagttggtgg cctgaatgac    600

aagaattgca caggaaaacg tgttctaatc ttaggcgctt caggcggagt tggtactttt    660

gctatacagg taatgaaagc atgggatgct catgtgacag cagtttgctc ccaagatgcc    720

agtgaacttg taaggaagct tggtgcagac gatgtaattg attacaaatc tggaagtgtg    780

gaagagcagt tgaaatcctt aaaaccattt gattttatcc ttgataatgt tggcggatcc    840

actgaaacat gggctccaga ttttctcaag aaatggtcag gagccaccta tgtgactttg    900

gtgactcctt tcctcctgaa catggaccga ttgggcatag cagatggcat gttgcagaca    960

ggagtcactg taggttcaaa ggcattaaag catttctgga aaggagtcca ttatcgctgg   1020

gcatttttca tggccagtgg cccatgttta gatgacattg cagaactggt ggatgcggga   1080

aagatccggc cagttattga acaaaccttt cctttttcta aagttccaga agccttcctg   1140

aaggtggaaa gaggacacgc acgaggaaag actgtaatta atgttgtt               1188
```

<210> SEQ ID NO 10
<211> LENGTH: 20
<212> TYPE: PRT
<213> ORGANISM: Synthetic Amino Acid Motif

<400> SEQUENCE: 10

```
Cys Lys Val Val Gln Lys Pro Ser Val Arg Arg Ile Ser Thr Thr Ser
1               5                   10                  15

Pro Arg Ser Thr
            20
```

<210> SEQ ID NO 11
<211> LENGTH: 20
<212> TYPE: PRT
<213> ORGANISM: Synthetic Amino Acid Motif

<400> SEQUENCE: 11

```
Cys Tyr Lys Ser Gly Ser Val Glu Glu Gln Leu Lys Ser Leu Lys Pro
1               5                   10                  15

Phe Asp Phe Ile
            20
```

<210> SEQ ID NO 12
<211> LENGTH: 20
<212> TYPE: PRT
<213> ORGANISM: Synthetic Amino Acid Motif

<400> SEQUENCE: 12

```
Cys Gly Gly Ser Thr Glu Thr Trp Ala Pro Asp Phe Leu Lys Lys Trp
1               5                   10                  15

Ser Gly Ala Thr
            20
```

<210> SEQ ID NO 13
<211> LENGTH: 30
<212> TYPE: PRT
<213> ORGANISM: Alcohol Dehydrogenase

<400> SEQUENCE: 13

```
Thr Cys Ala Val Phe Gly Leu Gly Gly Val Gly Leu Ser Val Ile Met
1               5                   10                  15

Gly Cys Lys Ala Ala Gly Ala Ala Arg Ile Ile Gly Val Asp
            20                  25                  30
```

-continued

<210> SEQ ID NO 14
<211> LENGTH: 31
<212> TYPE: PRT
<213> ORGANISM: Lactate Dehydrogenase

<400> SEQUENCE: 14

```
Lys Ile Thr Val Val Gly Val Gly Ala Val Gly Met Ala Cys Ala Ile
1               5                   10                  15

Ser Ile Leu Met Lys Asp Leu Ala Asp Glu Val Ala Leu Val Asp
            20                  25                  30
```

<210> SEQ ID NO 15
<211> LENGTH: 29
<212> TYPE: PRT
<213> ORGANISM: Glyceraldehydephosphate Dehydrogenase

<400> SEQUENCE: 15

```
Lys Val Cys Ile Val Gly Ser Gly Asp Trp Gly Ser Ala Ile Ala Lys
1               5                   10                  15

Ile Val Gly Gly Asn Ala Ala Gln Leu Ala Gln Phe Asp
            20                  25
```

<210> SEQ ID NO 16
<211> LENGTH: 33
<212> TYPE: PRT
<213> ORGANISM: Human p43

<400> SEQUENCE: 16

```
Arg Val Leu Ile Leu Gly Ala Ser Gly Gly Val Gly Thr Phe Ala Ile
1               5                   10                  15

Gln Val Met Lys Ala Trp Asp Ala His Val Thr Ala Val Cys Ser Gln
            20                  25                  30

Asp
```

<210> SEQ ID NO 17
<211> LENGTH: 33
<212> TYPE: PRT
<213> ORGANISM: Mouse p43

<400> SEQUENCE: 17

```
Arg Ala Leu Ile Leu Gly Ala Ser Gly Gly Val Gly Thr Phe Ala Ile
1               5                   10                  15

Gln Val Met Lys Ala Trp Gly Ala His Val Thr Ala Val Cys Ser Lys
            20                  25                  30

Asp
```

<210> SEQ ID NO 18
<211> LENGTH: 5
<212> TYPE: PRT
<213> ORGANISM: Conserved Amino Acid Motif
<220> FEATURE:
<223> OTHER INFORMATION: WS Motif
<221> NAME/KEY: UNSURE
<222> LOCATION: (3)..(3)
<223> OTHER INFORMATION: Xaa represents any amino acid

<400> SEQUENCE: 18

```
Trp Ser Xaa Trp Ser
```

IL-2R-ASSOCIATED POLYPEPTIDE AND DNA MOLECULES CODING THEREFOR

FIELD OF THE INVENTION

The present invention relates to the polypeptide p43, to polypeptides which contain binding sites for at least two of $NAD^+$, interleukin 2 receptor (IL-2R) β-chain, or IL-2R γ-chain, to nucleic acid molecules containing the coding information for the aforementioned polypeptides, to antibodies specific for the aforementioned polypeptides, to antisense oligonucleotides, to pharmaceutical compositions containing the aforementioned polypeptides or nucleic acids, and to methods of producing the aforementioned polypeptides.

BACKGROUND OF THE INVENTION

Interleukin 2 (IL-2) plays a critical role in the regulation of proliferation and differentiation of hematopoietic cells (27, 29). IL-2 exerts its multiple biological activities through its binding to a specific cell surface receptor (IL-2R) (30), including protein tyrosine kinase (PTK) activation, and nuclear proto-oncogene expression which may be critical for cellular proliferation (16, 29). IL-2R contains at least three distinct subunits; the α-chain, the β-chain and the γ-chain (5, 9, 28). Among these subunits, both the IL-2R β- and γ-chains belong to a newly identified superfamily of cytokine receptors, characterized by four conserved cysteines and the sequence Trp-Ser-X-Trp-Ser (the "WS motif SEQ ID NO: 18") in their extracellular domains (1, 2). Notably, none of the IL-2R subunits possesses any known catalytic activity such as PTK activity.

The expression of different combinations of the IL-2R subunits gives rise to various forms of IL-2R, each of which exhibiting different binding affinity to IL-2 (28). The "high-affinity" IL-2R (Kd; $10^{-11}$) consists of the heterotrimer α-, β- and γ-chains, the "intermediate-affinity" IL-2R (Kd; $10^{-9}$) results from the heterodimer β- and γ-chains, whereas the "low-affinity" IL-2R (Kd; $10^{-8}$) can be generated by expression of the α-chain alone. IL-2R β-chain possesses the largest cytoplasmic domain, consisting of 288 amino acids (a.a.) and was shown to play a critical role in IL-2 signal transduction (8). When the human IL-2R β-chain cDNA was introduced into murine IL-3-dependent pro-B cell line BAF-B03, which normally expresses the endogenous IL-2R α- and γ-chains, but not the β-chain, these cells were capable of proliferating in response to IL-2 (3, 8). Further expression studies with deletion mutant cDNAs of the IL-2R β-chain revealed that a restricted cytoplasmic region of the IL-2R β-chain, designated the "serine-rich" region (S-region), is indispensable for c-myc gene induction and for mitogenesis following IL-2 stimulation of the BAF-B03 cells (26). Another cytoplasmic region of the IL-2R β-chain, rich in acidic amino acids, designated the "acidic" region (A-region), is required in addition to the S-region for the src-family PTK activation and $p21^{iras}$ activation and for c-foslc-jun gene induction following IL-2 stimulation of BAF-B03 cells (6, 7, 17, 24, 26). Several lines of evidence suggest that the IL-2R γ-chain may also be critical for IL-2-induced signal transduction (29). Moreover, IL-2R γ-chain is suggested to be a shared common component among the IL-2, IL-4 and IL-7 receptors and possibly other cytokine receptors (14, 15, 21, 23). Mutations of IL-2R γ-chain have been found in X-linked severe combined immunodeficiency patients who show defects in T-cell development (22), providing evidence for the critical role of IL-2R γ-chain in cytokine signaling. Furthermore, recent studies have indicated that the functional cooperation between the cytoplasmic domains of IL-2R β-chain and γ-chain is critical for IL-2 signaling (11, 19, 20).

Because of the importance of IL-2R-mediated processes for normal body functions and disease, there is a need of better understanding of these processes as well as the need of new tools for influencing them.

SUMMARY OF THE INVENTION

The present invention provides a new IL-2R-associated protein, p43, and nucleic acid molecules containing the coding information for p43. Preferably, the p43 polypeptide has the amino acid sequence of SEQ ID NO: 2 (cf. FIGS. 1A–1B):

```
Met Glu Phe Leu Lys Thr Cys Val Leu Arg Arg Asn Ala Cys Thr

Ala Val Cys Phe Trp Arg Ser Lys Val Val Gln Lys Pro Ser Val

Arg Arg Ile Ser Thr Thr Ser Pro Arg Ser Thr Val Met Pro Ala

Trp Val Ile Asp Lys Tyr Gly Lys Asn Glu Val Leu Arg Phe Thr

Gln Asn Met Met Met Pro Ile Ile His Tyr Pro Asn Glu Val Ile

Val Lys Val His Ala Ala Ser Val Asn Pro Ile Asp Val Asn Met

Arg Ser Gly Tyr Gly Ala Thr Ala Leu Asn Met Lys Arg Asp Pro

Leu His Val Lys Ile Lys Gly Glu Glu Phe Pro Leu Thr Leu Gly

Arg Asp Val Ser Gly Val Val Met Glu Cys Gly Leu Asp Val Lys

Tyr Phe Lys Pro Gly Asp Glu Val Trp Ala Ala Val Pro Pro Trp

Lys Gln Gly Thr Leu Ser Glu Phe Val Val Val Ser Gly Asn Glu

Val Ser His Lys Pro Lys Ser Leu Thr His Thr Gln Ala Ala Ser

Leu Pro Tyr Val Ala Leu Thr Ala Trp Ser Ala Ile Asn Lys Val

Gly Gly Leu Asn Asp Lys Asn Cys Thr Gly Lys Arg Val Leu Ile
```

-continued

Leu Gly Ala Ser Gly Gly Val Gly Thr Phe Ala Ile Gln Val Met
Lys Ala Trp Asp Ala His Val Thr Ala Val Cys Ser Gln Asp Ala
Ser Glu Leu Val Arg Lys Leu Gly Ala Asp Asp Val Ile Asp Tyr
Lys Ser Gly Ser Val Glu Glu Gln Leu Lys Ser Leu Lys Pro Phe
Asp Phe Ile Leu Asp Asn Val Gly Gly Ser Thr Glu Thr Trp Ala
Pro Asp Phe Leu Lys Lys Trp Ser Gly Ala Thr Tyr Val Thr Leu
Val Thr Pro Phe Leu Leu Asn Met Asp Arg Leu Gly Ile Ala Asp
Gly Met Leu Gln Thr Gly Val Thr Val Gly Ser Lys Ala Leu Lys
His Phe Trp Lys Gly Val His Tyr Arg Trp Ala Phe Phe Met Ala
Ser Gly Pro Cys Leu Asp Asp Ile Ala Glu Leu Val Asp Ala Gly
Lys Ile Arg Pro Val Ile Glu Gln Thr Phe Pro Phe Ser Lys Val
Pro Glu Ala Phe Leu Lys Val Glu Arg Gly His Ala Arg Gly Lys
Thr Val Ile Asn Val Val, or SEQ ID NO: 4 (cf FIG. 1C, mouse p43):

Met Gly Val Leu Lys Thr Cys Val Leu Arg Arg Ser Ala Cys Ala
Ala Ala Cys Phe Trp Arg Arg Thr Val Ile Pro Lys Pro Pro Phe
Arg Gly Ile Ser Thr Thr Ser Ala Arg Ser Thr Val Met Pro Ala
Trp Val Ile Asp Lys Tyr Gly Lys Asn Glu Val Leu Arg Phe Thr
Gln Asn Met Met Leu Pro Ile Ile His Tyr Pro Asn Glu Val Ile
Ile Lys Val His Ala Ala Ser Val Asn Pro Ile Asp Val Asn Met
Arg Ser Gly Tyr Gly Ala Thr Ala Leu Asn Met Lys Arg Asp Pro
Leu His Met Lys Thr Lys Gly Glu Glu Phe Prd Leu Thr Leu Gly
Arg Asp Val Ser Gly Val Val Met Glu Cys Gly Leu Asp Val Lys
Tyr Phe Gln Pro Gly Asp Glu Val Trp Ala Ala Val Pro Pro Trp
Lys Gln Gly Thr Leu Ser Glu Phe Val Val Val Ser Gly Asn Glu
Val Ser His Lys Pro Lys Ser Leu Thr His Thr Gln Ala Ala Ser
Leu Pro Tyr Val Ala Leu Thr Ala Trp Ser Ala Ile Asn Lys Val
Gly Gly Leu Ser Asp Arg Asn Cys Lys Gly Lys Arg Ala Leu Ile
Leu Gly Ala Ser Gly Gly Val Gly Thr Phe Ala Ile Gln Val Met
Lys Ala Trp Gly Ala His Val Thr Ala Val Cys Ser Lys Asp Ala
Ser Glu Leu Val Arg Lys Leu Gly Ala Asp Glu Val Ile Asp Tyr
Thr Leu Gly Ser Val Glu Glu Gln Leu Lys Ser Leu Lys Leu Cys
Ala Phe Ile Leu Asp Asn Val Gly Gly Ser Thr Glu Thr Trp Ala
Leu Asn Phe Leu Lys Lys Trp Ser Gly Ala Thr Tyr Val Thr Leu
Val Thr Pro Phe Leu Leu Asn Met Asp Arg Leu Gly Val Ala Asp
Gly Met Leu Gln Thr Gly Val Thr Val Gly Thr Lys Ala Met Lys
His Leu Trp Gln Gly Val His Tyr Arg Trp Ala Phe Phe Met Ala
Ser Gly Pro Tyr Leu Asp Glu Ile Ala Glu Leu Val Asp Ala Gly

-continued

Lys Ile Arg Pro Val Ile Glu Arg Thr Phe Pro phe Ser Glu Val

Pro Glu Ala Phe Leu Lys Val Glu Arg Gly His Ala Arg Gly Lys

Thr Val Val Asn Val Val.

The invention is further related to polypeptides with p43-like activity or functional derivatives of p43, especially polypeptides which contain a binding site for at least $NAD^+$ and IL-2R β-chain, $NAD^+$and IL-2R γ-chain, or IL-2R β-chain and IL-2R γ-chain. Functional derivatives may be variants, fragments, chemical derivatives, or fusion proteins of p43.

In a further aspect, the present invention is related to nucleic acid molecules containing the coding information for p43, polypeptides with p43-like activity, or functional derivatives. Preferably, a nucleic acid molecule according to the present invention is a nucleic acid molecule containing the nucleotide sequence of SEQ ID NO: 1 (cf. FIGS. 1A–1B):

AGAATGGACA GAATACTGAC TGGAACGTTA ATTCGAGCAT TTCATATGCG

AAGAGCGGAA TAACAGTTCC GTATTCTTCT TTCAGTTTCT CCATTAGATT

AGCTTCATTT TCGAAGGCTC CGTTTTGCAT GCTTAATTTT GAAACTAGCC

CGTGGTTTGG CAGAATTTGA CTGAATTCAG GGGTGAGAGT TTGATCCAGT

CCAAGTGTAT TTGAATTTGA GCACGCAGTT CAACCAGTGT TTACA

ATG GAA TTT CTG AAG ACT TGT GTA CTT AGA AGA AAT GCA TGC ACT

GCG GTT TGC TTC TGG AGA AGC AAA GTT GTC CAA AAG CCT TCA GTT

AGA AGG ATT AGT ACT ACC TCT CCA AGG AGC ACT GTC ATG CCT GCT

TGG GTG ATA GAT AAA TAT GGG AAG AAT GAA GTG CTT CGA TTC ACT

CAG AAC ATG ATG ATG CCT ATT ATA CAC TAT CCA AAT GAA GTC ATT

GTC AAA GTT CAC GCT GCC AGT GTA AAT CCT ATA GAC GTT AAT ATG

AGA AGT GGT TAT GGA GCT ACA GCT TTA AAT ATG AAG CGT GAT CCT

TTA CAC GTG AAA ATC AAA GGA GAA GAA TTT CCT CTG ACT CTG GGT

CGG GAT GTC TCT GGC GTG GTG ATG GAA TGT GGG CTT GAT GTG AAA

TAC TTC AAG CCT GGA GAT GAG GTC TGG GCT GCA GTT CCT CCT TGG

AAA CAA GGC ACT CTT TCA GAG TTT GTT GTA GTC AGT GGG AAT GAG

GTC TCT CAC AAA CCC AAA TCA CTC ACT CAT ACT CAA GCT GCC TCT

TTG CCA TAT GTG GCT CTC ACA GCC TGG TCT GCT ATA AAC AAA GTT

GGT GGC CTG AAT GAC AAG AAT TGC ACA GGA AAA CGT GTT CTA ATC

TTA GGC GCT TCA GGC GGA GTT GGT ACT TTT GCT ATA CAG GTA ATG

AAA GCA TGG GAT GCT CAT GTG ACA GCA GTT TGC TCC CAA GAT GCC

AGT GAA CTT GTA AGG AAG CTT GGT GCA GAC GAT GTA ATT GAT TAC

AAA TCT GGA AGT GTG GAA GAG CAG TTG AAA TCC TTA AAA CCA TTT

GAT TTT ATC CTT GAT AAT GTT GGC GGA TCC ACT GAA ACA TGG GCT

CCA GAT TTT CTC AAG AAA TGG TCA GGA GCC ACC TAT GTG ACT TTG

GTG ACT CCT TTC CTC CTG AAC ATG GAC CGA TTG GGC ATA GCA GAT

GGC ATG TTG CAG ACA GGA GTC ACT GTA GGT TCA AAG GCA TTA AAG

CAT TTC TGG AAA GGA GTC CAT TAT CGC TGG GCA TTT TTC ATG GCC

AGT GGG CCA TGT TTA GAT GAC ATT GCA GAA CTG GTG GAT GCG GGA

AAG ATC CGG CCA GTT ATT GAA CAA ACC TTT CCT TTT TCT AAA GTT

-continued

CCA GAA GCC TTC CTG AAG GTG GAA AGA GGA CAC GCA CGA GGA AAG

ACT GTA ATT AAT GTT GTT TAAATAAAAA TGCAGTTTAG TGATTAAAAA

AAAAAAAAAA AAAAAAAA, or a degenerate variant of said nucleic acid molecule containing the nucleotide sequence of SEQ ID NO: 1, or a nucleic acid molecule capable of hybridizing to a nucleic acid molecule having SEQ ID NO: 1, or a nucleic acid molecule containing a part of the nucleotide sequence of any of the foregoing nucleic acid molecules, or a fragment of any one of the foregoing nucleic acid molecules. Preferably, such a nucleic acid molecule containing a part of SEQ ID NO: 1 contains the nucleotide sequence of SEQ ID NO: 9:

ATG GAA TTT CTG AAG ACT TGT GTA CTT AGA AGA AAT GCA TGC ACT

GCG GTT TGC TTC TGG AGA AGC AAA GTT GTC CAA AAG CCT TCA GTT

AGA AGG ATT AGT ACT ACC TCT CCA AGG AGC ACT GTC ATG CCT GCT

TGG GTG ATA GAT AAA TAT GGG AAG AAT GAA GTG CTT CGA TTC ACT

CAG AAC ATG ATG ATG CCT ATT ATA CAC TAT CCA AAT GAA GTC ATT

GTC AAA GTT CAC GCT GCC AGT GTA AAT CCT ATA GAC GTT AAT ATG

AGA AGT GGT TAT GGA GCT ACA GCT TTA AAT ATG AAG CGT GAT CCT

TTA CAC GTG AAA ATC AAA GGA GAA GAA TTT CCT CTG ACT CTG GGT

CGG GAT GTC TCT GGC GTG GTG ATG GAA TGT GGG CTT GAT GTG AAA

TAC TTC AAG CCT GGA GAT GAG GTC TGG GCT GCA GTT CCT CCT TGG

AAA CAA GGC ACT CTT TCA GAG TTT GTT GTA GTC AGT GGG AAT GAG

GTC TCT CAC AAA CCC AAA TCA CTC ACT CAT ACT CAA GCT GCC TCT

TTG CCA TAT GTG GCT CTC ACA GCC TGG TCT GCT ATA AAC AAA GTT

GGT GGC CTG AAT GAC AAG AAT TGC ACA GGA AAA CGT GTT CTA ATC

TTA GGC GCT TCA GGC GGA GTT GGT ACT TTT GCT ATA CAG GTA ATG

AAA GCA TGG GAT GCT CAT GTG ACA GCA GTT TGC TCC CAA GAT GCC

AGT GAA CTT GTA AGG AAG CTT GGT GCA GAC GAT GTA ATT GAT TAC

AAA TCT GGA AGT GTG GAA GAG CAG TTG AAA TCC TTA AAA CCA TTT

GAT TTT ATC CTT GAT AAT GTT GGC GGA TCC ACT GAA ACA TGG GCT

CCA GAT TTT CTC AAG AAA TGG TCA GGA GCC ACC TAT GTG ACT TTG

GTG ACT CCT TTC CTC CTG AAC ATG GAC CGA TTG GGC ATA GCA GAT

GGC ATG TTG CAG ACA GGA GTC ACT GTA GGT TCA AAG GCA TTA AAG

CAT TTC TGG AAA GGA GTC CAT TAT CGC TGG GCA TTT TTC ATG GCC

AGT GGC CCA TGT TTA GAT GAC ATT GCA GAA CTG GTG GAT GCG GGA

AAG ATC CGG CCA GTT ATT GAA CAA ACC TTT CCT TTT TCT AAA GTT

CCA GAA GCC TTC CTG AAG GTG GAA AGA GGA CAC GCA CGA GGA AAG

ACT GTA ATT AAT GTT GTT, or a degenerate variant of SEQ ID NO: 9.

Preferably, a nucleic acid molecule according to the present invention is capable of hybridizing to a nucleic acid molecule having the nucleotide sequence of SEQ ID NO: 1 under conditions which select for a homology, or sequence identity, of more than 50%, more preferably more than 70%, more preferably more than 80%, more preferably more than 90%. Preferably, such nucleic acid molecules capable of hybridizing contain the coding information for polypeptides with p43-like biological and/or immunological activity, said polypeptides, more preferably, having at least one of the binding sites of p43 for $NAD^+$, IL-2R β-chain, or IL-2R γ-chain, more preferably at least two of said binding sites.

A further aspect of the present invention is a vector containing the nucleotide sequence of any one of the foregoing nucleic acids, especially when said nucleotide sequence is operationally linked to an expression control sequence as in expression vectors.

A further aspect of the present invention is a host cell carrying a vector as described, especially an expression vector. Such a host cell can be a procaryotic or eucaryotic cell. Preferably, such a host cell is a bacterial cell, a yeast cell, or a mammalian cell. More preferably, said host cell is an *E. coli* cell or a COS cell.

Accordingly, a still further aspect of the present invention is a method of production of p43, functional derivatives of p43, or polypeptides with p43-like activity, by recombinant expression. Such a method is characterized by cultivating a host cell as described, said host cell carrying an expression vector containing the coding information for p43, a functional derivative of p43, or a polypeptide with p43-like biological activity, under conditions where said coding information is expressed by said host cell, and isolating the expressed polypeptide.

A further aspect of the present invention is an antibody molecule specific for p43, a functional derivative of p43, or a polypeptide with p43-like activity. Such an antibody molecule can be a polyclonal or monoclonal antibody, a complete immunoglobulin or a fragment thereof, especially a Fab' or $F(ab)_2$ fragment, a recombinant antibody or antibody fragment, for example a recombinant single-chain antibody (scFv), a chimeric, bispecific or humanised antibody.

Preferably, such an antibody molecule is specific for one of the following amino acid sequences:

SEQ ID NO:10: CKVVQKPSVRRISTTSPRST

SEQ ID NO:11: CYKSGSVEEQLKSLKPFDFI

SEQ ID NO:12: CGGSTETWAPDFLKKWSGAT,

SEQ ID NO: 11 being preferred.

A still further aspect of the present invention is an antisense oligonucleotide corresponding to a part of the nucleotide sequence of any nucleic acid molecule according to the present invention. One preferred embodiment of such an oligonucleotide has the sequence SEQ ID NO: 8: 5'-GTCTTCAAAACGCCCATCCT-3'.

A still further aspect of the present invention is a pharmaceutical composition containing p43, a functional derivative of p43, or a polypeptide with p43-like activity, or a nucleic acid containing the coding information for any one of the foregoing polypeptides, or an oligonucleotide corresponding to a part of the nucleotide sequence of said nucleic acid molecule. Such a pharmaceutical composition can be used for the treatment and diagnosis of IL-2-related disorders.

DESCRIPTION OF THE PREFERRED EMBODIMENTS

As used herein, a "polypeptide with p43-like activity" is a polypeptide which exhibits a biological activity which is essentially similar to p43. This means that is has one or more, preferably at least two of its structural or catalytic properties in common with p43, for example with respect to the binding properties of p43 to $NAD^+$, IL-2R β-chain, and/or IL-2R γ-chain. As used herein, a "functional derivative" of p43 is a compound which possesses a biological activity (either functional or structural) that is substantially similar to a biological activity of p43. Examples of biological activities include the ability to bind to a natural ligand of p43, preferably to bind at least two of $NAD^+$, IL-2R β-chain, or IL-2R γ-chain. A molecule is said to be "substantially similar" to another molecule if both molecules have substantially similar structures or if both molecules possess a similar biological activity. The "functional derivatives" of p43 include fragments, variants, chemical derivatives or fusion proteins of p43. The term "fragment of p43" is meant to refer to any polypeptide subset of that molecule. The term "variant of p43" is meant to refer to a molecule substantially similar in structure to either the entire molecule, or to a fragment thereof, provided that the variant has at least one biological activity that is either similar to an activity of p43 or inhibitory to an activity of p43. A variant of p43 may differ from p43 by the substitution, deletion or addition of one or more amino acids, preferably 1 to 10 amino acids. Preferably, a variant has the ability to bind at least two of $NAD^+$, IL-2R β-chain, or IL-2R γ-chain. A "chemical derivative of p43" is a molecule which has been derived from p43 by a chemical reaction, for example iodination, acetylation, or linkage to a radioisotope or toxin. A "fusion protein of p43" is a polypeptide which has been generated by recombinant expression of all or a part of the p43 gene fused to all or part of another gene or nucleic acid containing in-frame coding information. A "degenerate variant" of a nucleic acid molecule is a second nucleic acid molecule which has a different nucleotide sequence as compared to the first nucleic acid molecule and codes for the same amino acid sequence as the first nucleic acid molecule, due to the degeneracy of the genetic code. A "fragment" of a nucleic acid molecule means a second nucleic acid molecule which has a nucleotide sequence representing a part of the nucleic acid sequence of the first nucleic acid molecule.

One way of carrying out the present invention is to isolate cDNAs whose protein products can interact with IL-2R γ-chain. To screen for human cDNA encoding proteins able to interact with IL-2R γ-chain, the two hybrid screening procedure described by (37) and (4) can be employed. In principle, DNA coding for IL-2R γ-chain (28), or a part of it, is fused to a DNA coding for the N-terminal domain of the *Saccharomyces cerevisiae* GAL4 protein, said N-terminal domain being capable of binding to specific DNA sequences ($UAS_G$). This construct can then be incorporated into an expression vector and transformed into a yeast strain which is deficient in GAL4. A cDNA collection which is to be screened can be incorporated into an expression vector, wherein the individual cDNA molecules are fused to DNA coding for the transcriptional activation domain of GAL4. The resulting constructs are transformed into the same yeast strain which has been pretransformed with the IL-2R γ-chain construct. In yeast cells which carry the cDNAs of interest, namely cDNAs coding for polypeptides able to bind to IL-2R γ-chain, those molecules bind to the IL-2R γ-chain polypeptides which are expressed in the same cell, thus bringing the two GAL4 domains (the DNA binding domain fused to IL-2R γ-chain and the transcriptional activation domain fused to the cDNA of interest) together. As a result of this interaction, transcription of genes regulated by GAL4/$UAS_G$ occurs. This can be employed for a suitable selection system, for example using the well-known β-galactosidase/galactose system. For example, LexA protein and IL-2R γ-chain fused gene can be constructed and transformed into appropriate yeast cells. The resultant transformant cell can be sequentially transformed with a pACT human cDNA library (4), and transformants can be subjected to the screening procedure. Transformants can be placed under selection, and surviving colonies can be screened for their ability to produce β-galactosidase. Positive clones consisting of a partial open reading frame fused to the GAL4 transcriptional activation domain can be identified. Using the cDNA insert of such a positive clone as probe, the overlapping cDNAs can be obtained. A full-length cDNA clone may be obtained or constructed from overlapping fragments by standard procedures. cDNAs obtained this way can then be used to screen other cDNA libraries, for example from other species like mouse, to identify related polypeptides. This can be performed by standard procedures as well.

Given the information of the present invention, especially the sequence information according to FIGS. 1A–1B and FIG. 1C, the polypeptides and nucleic acid molecules of the present invention can be produced by standard procedures. A nucleic acid molecule with the nucleotide sequence according to FIGS. 1A–1B, for example, can be produced by chemical synthesis. An alternative way would be to chemically synthesize an oligonucleotide or DNA fragment corresponding to a part of the nucleotide sequence as outlined in FIGS. 1A–1B and to screen an appropriate cDNA library or genomic library by hybridization. Detailed protocols how to design such an oligonucleotide or DNA fragment, how to generate a library, and how to screen such a library by hybridization with the oligonucleotide or DNA fragment can be found in standard laboratory manuals, for example in (32), especially in chapters 7, 8, 9, 11 and 12, the content of which shall be incorporated into this specification by reference. Therein, it is also taught how to adjust the appropriate hybridization conditions for a given probe, for example conditions which select for perfect matching (homology of 100%), or conditions which select for homologies of 50%, 70%, 80% or 90% (32, pages 11.45–11.57). As an example, using a human p43 cDNA as a probe, hybridization in 3×SSC at 65° C. could select mouse p43 cDNA which has a homology of about 90% on the amino acid level. Alternatively, a nucleic acid containing the coding information for p43, or a fragment thereof, can be generated from a cDNA library by polymerase chain reaction according to standard laboratory protocols (32, chapter 14).

With a nucleic acid coding for p43 or a functional derivative thereof in hands, especially the coding sequence according to FIGS. 1A–1B (starting with A at position 246 and ending with T at position 1433 of the nucleotide sequence of FIGS. 1A–1B), the expert can produce the polypeptide by recombinant expression according to standard protocols either in procaryotic or eucaryotic host cells (see, for example, 32, especially chapters 16 and 17). For this purpose, the nucleic acid molecule containing the coding sequence of interest is incorporated into an expression vector where it is operationally linked to an expression control sequence. This expression vector is adapted to the special requirements of the host cell of choice. Expression may be regulatable. The expression vector is then introduced into the host cell of choice. Upon cultivation under appropriate conditions, the host cells synthesize the p43 polypeptide or functional derivative thereof. The expression system may permit secretion of the expressed polypeptide into the culture medium. The polypeptide can then be isolated from either the host cells or, when the expressed polypeptide is secreted into the medium, from the culture medium. Specific examples for the expression of p43 or is functional derivatives thereof are described below.

Given the information of the present invention, especially the sequence information of FIGS. 1A–1B, the expert may construct functional derivatives of p43. This can be achieved by constructing a DNA molecule containing the coding information for a functional derivative, incorporating this DNA molecule into an expression vector, introducing this expression vector into a host cell and then expressing said DNA molecule coding for said functional derivative. For example, the expert can produce a fragment of a DNA molecule coding for p43, said DNA fragment containing only a part of the complete sequence, and express this fragment. For a functional analysis of the resulting polypeptide fragment, the expert can perform binding studies with the natural ligands of p43, $NAD^+$, IL-2R β-chain, or IL-2R γ-chain, either as described below, or with similar methods. Preferably, fragments of p43 retain at least one, more preferably at least two of the binding sites for $NAD^+$, IL-2R β-chain, or IL-2R γ-chain. For the production of variants, the expert can modifiy a DNA molecule containing all or part of the complete coding information for p43 by standard procedures, for example site-directed mutagenesis (32, especially chapter 15; 33, chapter 11, p 279–295), and express the thus modified DNA molecule as described. As an example, variants may be characterized by substitution, insertion or deletion of one, two, three, or more amino acids, as compared to p43 as described. After expression, the thus generated variant polypeptide can be tested whether it is functional as described. For the production of chemical derivatives of a given polypeptide, standard procedures may be used as well (see, for example, 33, chapter 9, p 225–245, and chapter 10, p 247–277). The generation of fusion proteins is described in the examples below.

Given the information of the present invention, especially the sequence information according to FIGS. 1A–1B, the expert can produce antibodies specific for p43, or finctional derivatives thereof, according to standard procedures (34, especially vol. 1, chapters 2, 3, 4). For use as an antigen, for example, a synthetic peptide representing a part of the amino acid sequences of SEQ ID NO: 2 or 4, or FIGS. 1A–1B, can be synthesized and used in an immunization protocol, optionally linked to a carrier. Another example for generating an antigen is the recombinant expression of p43 or a functional derivative thereof, optionally as a fusion protein, for example in *E. coli*. The expressed polypeptide or fusion protein—optionally purified—can then be used in an immunization scheme. Specific antibodies or—in the case of monoclonal antibodies—hybridomas which produce specific antibodies can then be selected by appropriate methods (35). Antibodies may either be monoclonal or polyclonal. Instead of an intact immunglobulin, fragments of immunglobulins may be used, for example Fab' or $F(ab)_2$ fragments. The production of recombinant antibodies or antibody fragments, chimeric antibodies, humanised antibodies, bispecific antibodies or single-chain antibodies for a given antigen are state of the art. Antibodies may be coupled to other agents, for example radioisotopes or toxins. Antibodies specific for p43, or finctional derivatives thereof, are useful tools for studying the mechanism of IL-2-induced cellular events or can be used to block or impair the transmission of the IL-2-induced signal.

Antisense oligonucleotides can be chemically synthesized according to standard procedures.

P43, functional derivatives thereof, nucleic acids containing the coding information for p43 or functional derivatives thereof, antibodies specific for p43 or fuictional derivatives thereof, or antisense oligonucleotides corresponding to parts of the nucleotide sequence coding for p43 or functional derivatives thereof can be used as drugs for the manufacture of pharmaceutical compositions for therapy or diagnosis of IL-2-related disorders. The molecules of the present invention can be formulated according to known methods, wherein these materials are combined in admixture with a pharmaceutically acceptable carrier vehicle. Suitable vehicles, and their formulation, optionally with other human proteins included, e.g. human serum albumin, are described, for example, in (36). The pharmaceutical compositions may be administered to patients intravenously, intramuscularly, subcutaneously, enterally, or parenterally. Administration may be by continous infusion, or by single or multiple boluses. The dosage will vary depending upon such factors as the patients age, weight, height, sex, general medical condition, disease, etc. In general, it will be in the range of from about 1 pg/kg body weight to 10 mg/kg body weight of patient.

Recombinantly produced p43 or functional derivatives thereof may be also used to study the mechanism of IL-2-induced signal transduction.

BRIEF DESCRIPTION OF THE DRAWINGS

FIGS. 1A–1C depicts the nucleotide sequence and complete predicted amino acid sequence of p43. (A–B) The nucleotide (SEQ ID NO:1) and predicted amino acid (SEQ ID NO:2) sequence of human p43. The amino acid sequence is indicated in single-letter code. Conserved residues of predicted $NAD^+$ binding domain are underlined. Nucleotide numbers are on the left, and amino acid numbers on the right. (C) Alignment of human (SEQ ID NO: 2) and mounse p43 (SEQ ID NO: 4) amino acid sequences. The region of predicted $NAD^+$binding domain shown is boxed.

EXAMPLES

Example 1

Two Hybrid Screening and cDNA Isolation

Figure 2:
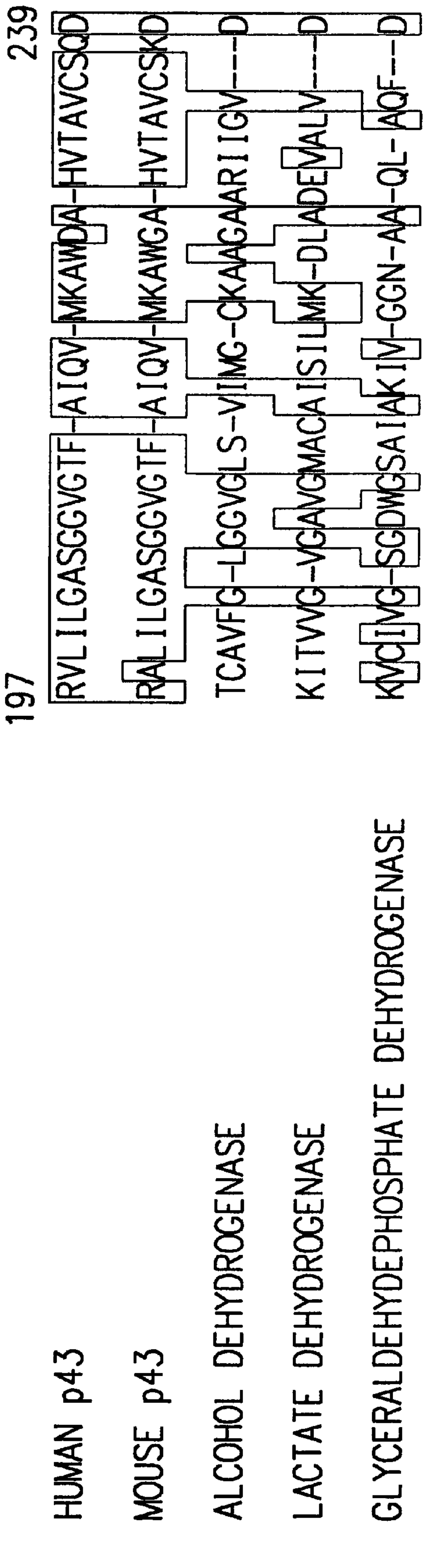
FIG. 2. Depicts the homology between p43 and Dehydrogenase members. Sequences of Alcohol dehydrogenase, (SEQ ID NO:13) Lactate dehydrogenase (SEQ ID NO:14) and Glyceraldehydephosphate dehydrogenase (SEQ ID NO:15) are aligned to human (SEQ ID NO:16) or mouse p43; (SEQ. ID NO:17) numbering is with respect to human p43. Identity with human or mouse p43 is indicated in open boxes.

Unless otherwise indicated, the protocol was adapted according to (4). For yeast two-hybrid screening, the open reading frame of human IL-2R γ-chain cytoplasmic region (28) was fused to the LexA DNA binding domain in the vector pBTM116 (4) by the following procedure; synthesized oligonucleotide primers (sense: SEQ ID NO: 5: 5'-ATTTCCCGGGGGAACGGACGATGCCCCGAA-3', antisense: SEQ ID NO: 6: 5'-CTTCTGTCGACGGATTGGGGTTCAGGTTTC-3'), which contained SmaI or SaI site, respectively, were used for PCR amplification of the cDNA encoding IL-2R γ-chain cytoplasmic region. The fragment was cut by SmaI and SaI and ligated with pBTM116. The resultant plasmid was cut by PstI and ligated to remove the C-terminal half region of γ-chain. The resultant plasmid was transformed into the CTYLD yeast strain as bait. This transformant strain was sequentially transformed with a B-cell derived pACT human cDNA library (4) which was kindly obtained from Dr. S. Elledge, and $1\times10^6$ transformants were analyzed by the standard method as described (4). Rare surviving colonies were screened for their ability to produce β-galactosidase. One positive clone was identified. Sequence analysis of the clone termed clone 36 encodes a partial open reading frame of ~1.4 kb fused to the GAL4 transcriptional activation domain. Using this, insert as probe, a human cDNA library generated from Jurkat cell mRNA was screened to obtain a full length cDNA for p43 coding sequence. For the isolation of the human full length cDNA, the λgt11 cDNA library was prepared with poly (A)+RNA from TPA-induced Jurkat cells (a human T cell leukemia line), according to standard procedures (32). For screening, probe DNA was prepared by XhoI enzyme treatment (cutting) of p43 cDNA obtained in the two hybrid screening. Five overlapping clones were characterized and found to possess inserts from 0.5–2 kb. DNA sequencing was carried out using the dideoxynucleotide chain termination method. The clone representing the longest insert coding sequence was sequenced. The clone contained a 2.0 kb cDNA segment that overlapped about 1.4 kb with clone 36, extended about 0.6 kb further to the 5' end, and contained the AUG initiation codon. This revealed a potential open reading frame of 396 amino acid-polypeptide (FIGS. 1A–1B) with a predicted molecular size of 43 kd. We called this gene product, p43. A computer-assisted sequence search with the GenBank database revealed that the sequence of p43 bears no significant homology to any known protein, except a partial similarity in a $NAD^+$ binding domain.

In addition, to obtain the mouse p43 cDNA, a cDNA library generated from mouse spleen cells mRNA was utilized and screened with human p43 cDNA fragment as probe. For the isolation of mouse p43 cDNA clone, the hybridization was performed using the EcoRI-cleaved insert from the full length human p43 cDNA clone as a probe and using a mouse cDNA library as described (38), and the filters were washed in 3×SSC at 65° C. (SSC buffer was prepared according to ref. 32, p. B.12). Screening of the cDNA library from mouse spleen with human p43 cDNA yielded a clone of highly related sequence. The predicted human and mouse p43 amino acid sequences are highly related, showing ~90% identity at the protein level (FIG. 1C). The amino acid sequence of $NAD^+$ binding domain is conserved in both human and mouse p43 (FIG. 1C and FIG. 2).

Figure 3:
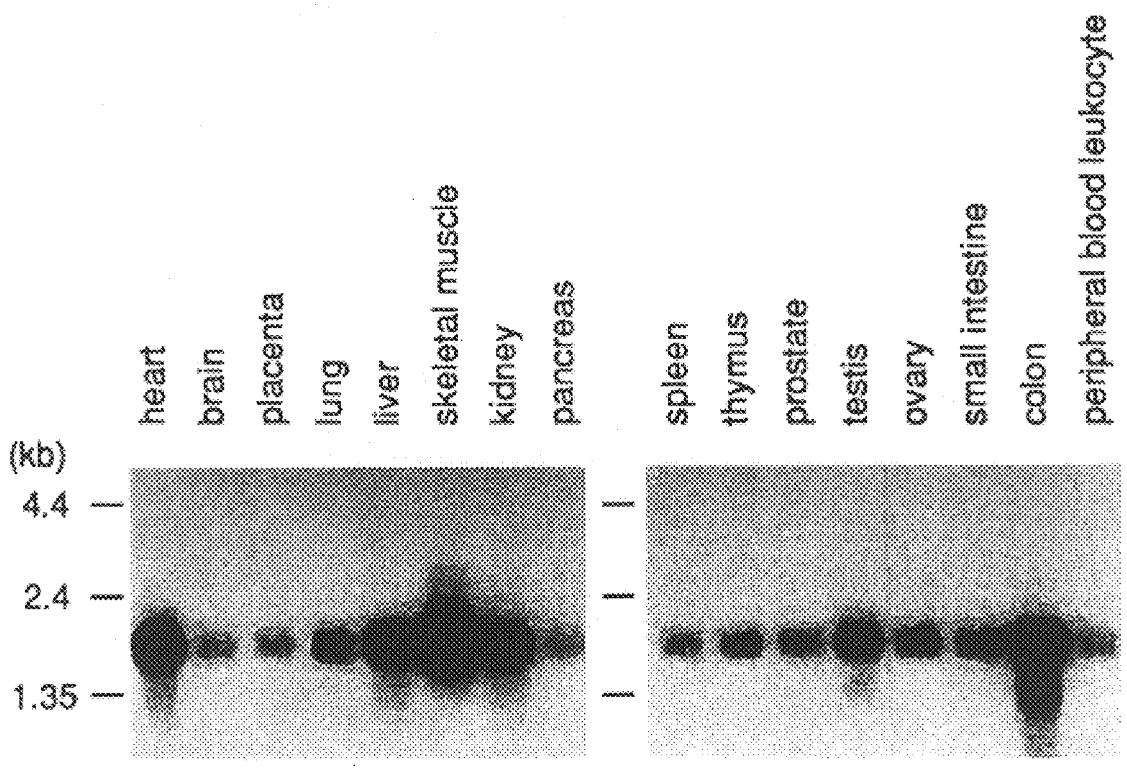
FIG. 3. Depicts a blot which shows the p43 mRNA expression in human tissues. Human tissue blot (Clontech, Palo Alto, Calf.). Molecular sizes are indicated on the left (in kilobases).

Expression of p43 mRNA detected by Northern blot analysis was ubiquitous to all human tissues tested. The p43 mRNA is approximately 2.0 kb in length and was most abundant in skeletal muscle (FIG. 3).

Example 2

Association of p43 with IL-2R γ-chain in Mammalian Cells

Figure 4A:
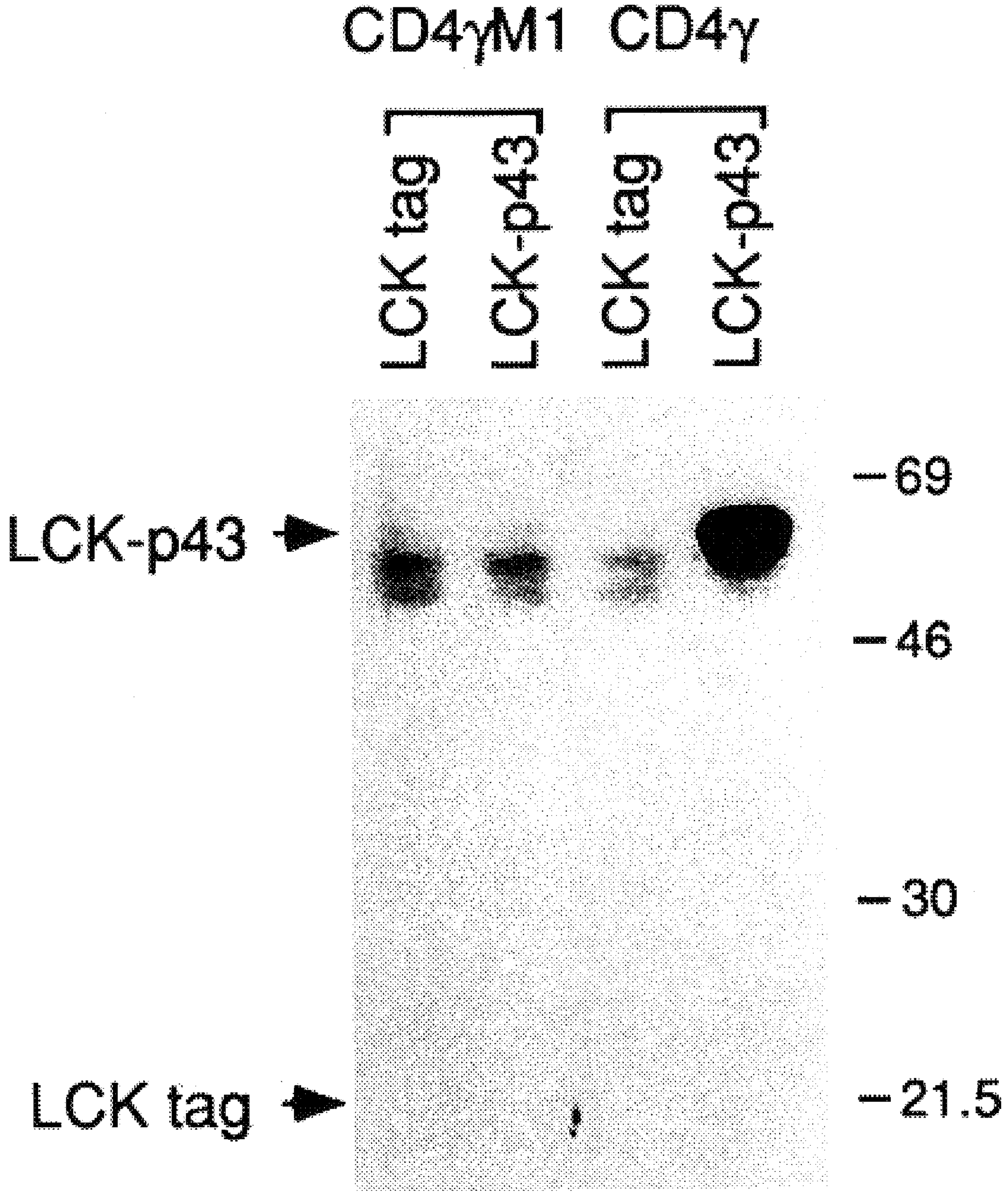
FIGS. 4A–4B. Depicts blots which show the association of p43 with IL-2R in COS cells. (A) Association of p43 with IL-2R γ-chain. Cell lysates were prepared from COS cells; COS cells transfected with CD4γ plus LCK tag, CD4γ plus LCK-p43, CD4γM1 plus LCK tag or CD4γM1 plus LCK-p43. Aliquots of the respective cell lysates were immunoprecipitated with anti-CD4 antibody (OKT4) followed by anti Lck immunoblotting. (B) Association of p43 with IL-2R β-chain. Cell lysates were prepared from COS cells; COS cells transfected with LCK-p43 plus CD4γ, CD4γM1, CD4β, CD4βA or CD4βS.

As mentioned above, we isolated an IL-2R γ-chain associated molecule, p43, using yeast two-hybrid system. However we did not know whether p43 can associate with IL-2R γ-chain in mammalian cells. To confirm the binding of p43 and IL-2R γ-chain in mammalian cells, we constructed two chimeric proteins linking p43 to the specific antibody recognized N-terminal region of $p56^{lck}$ (LCK-p43) and IL-2R γ-chain to the extracellular domain of CD4 (CD4γ). The expression plasmids, CD4γ and LCK-p43, were transiently co-transfected into monkey COS7 cells and then the intermolecular association was analyzed by immunoprecipitation with OKT4 and following western blotting analysis with anti-Lck antiserum (for details, see Example 6; see also ref. (7)). LCK-p43 and LCK tag were expressed in the transfected COS cells as assessed by anti-Lck antiserum immunoblotting of whole cell lysates (data not shown). FIG. 4A shows that IL-2R γ-chain bound to LCK-p43, but not to control LCK tag or the truncated IL-2R γ-chain, which contains only the transmembrane region, indicating a direct association of the two proteins in mammalian cells.

Example 3

IL-2R β-chain Also Associates with p43

Figure 4B:
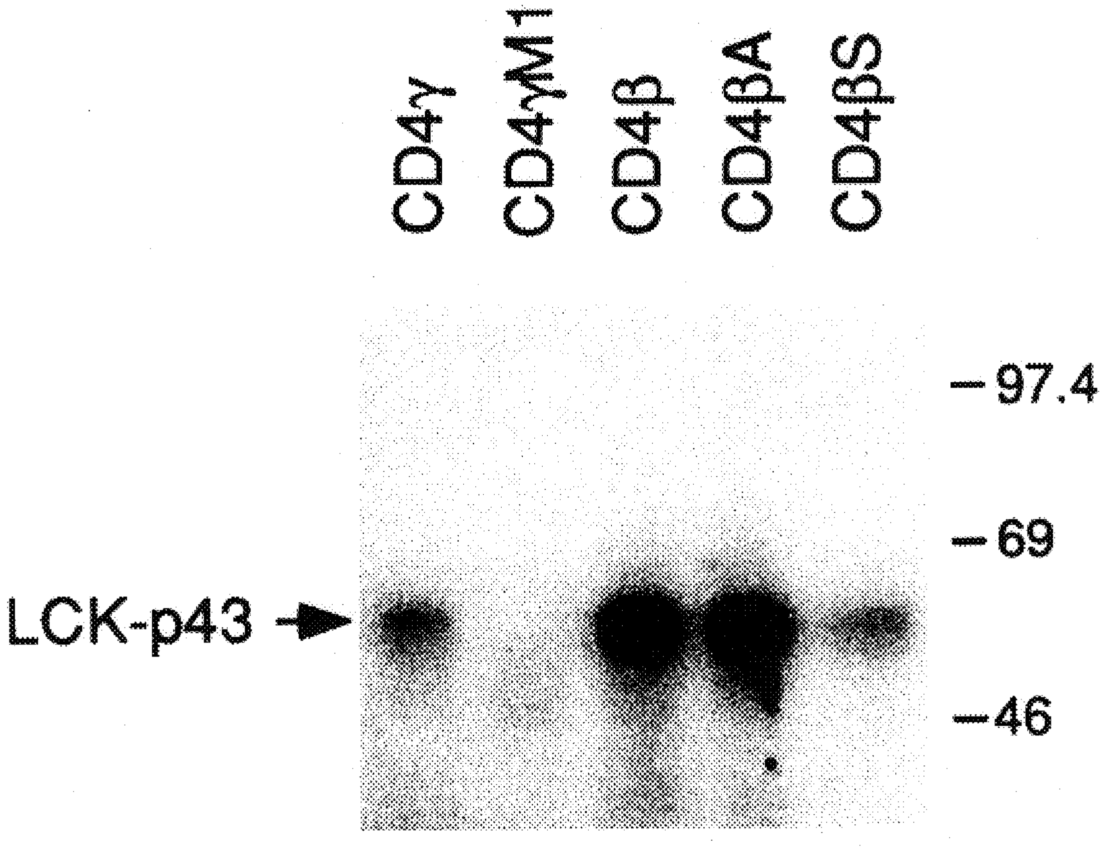

Because IL-2R γ-chain and β-chain are associated and share important functions in IL-2 signal transduction, we determined whether IL-2R β-chain also associates with p43. To confirm the association of these molecules, we further constructed the chimera genes fusing IL-2R β-chain, or mutant β-chain, to CD4 (CD4-IL-2Rβ, CD4-βS, CD4-βA). These plasmids and Lck-p43 were cotransfected into monkey COS7 cells and the intermolecular association measured (cf. Examples 2, 6). FIG. 4B shows that p43 can associate with not only IL-2R γ-chain but also IL-2R β-chain. Interestingly, the p43 was tightly associated with IL-2R β-chain through the S-region which is the critical region for IL-2-mediated signal transduction.

Example 4

Synthesis of Oligodeoxynucleotides and Measurement of $[^3H]$ Thymidine Incorporation S-oligodeoxynucleotides were synthesized on an automated DNA synthesizer (Applied Biosystems). The sequence of the sense and antisense oligodeoxynucleotides are: SEQ ID NO: 7: 5'-CAGGATGGGCGTTTTGAAGA-3' and SEQ ID NO: 8: 5'-GTCTTCAAAACGCCCATCCT-3', respectively. The FWT-2 cell, which is BAF-B03-derived cell line expressing wild-type human IL-2R β- and γ-chains, was used in this experiment. After continuously growing cells were washed with PBS, the cells were distributed into 96-well plates at an initial concentration of $1\times10^4$ per well. An oligomer (5 μM or 10 μM) was added with or without IL-2 (2 nM). After 20 hrs incubation, the cells were pulse-labeled with 1 μCi of $[^3H]$ thymidine (20 μCi/mmol) (NEN Research Products) 4 hrs prior to harvest.

Figure 5:
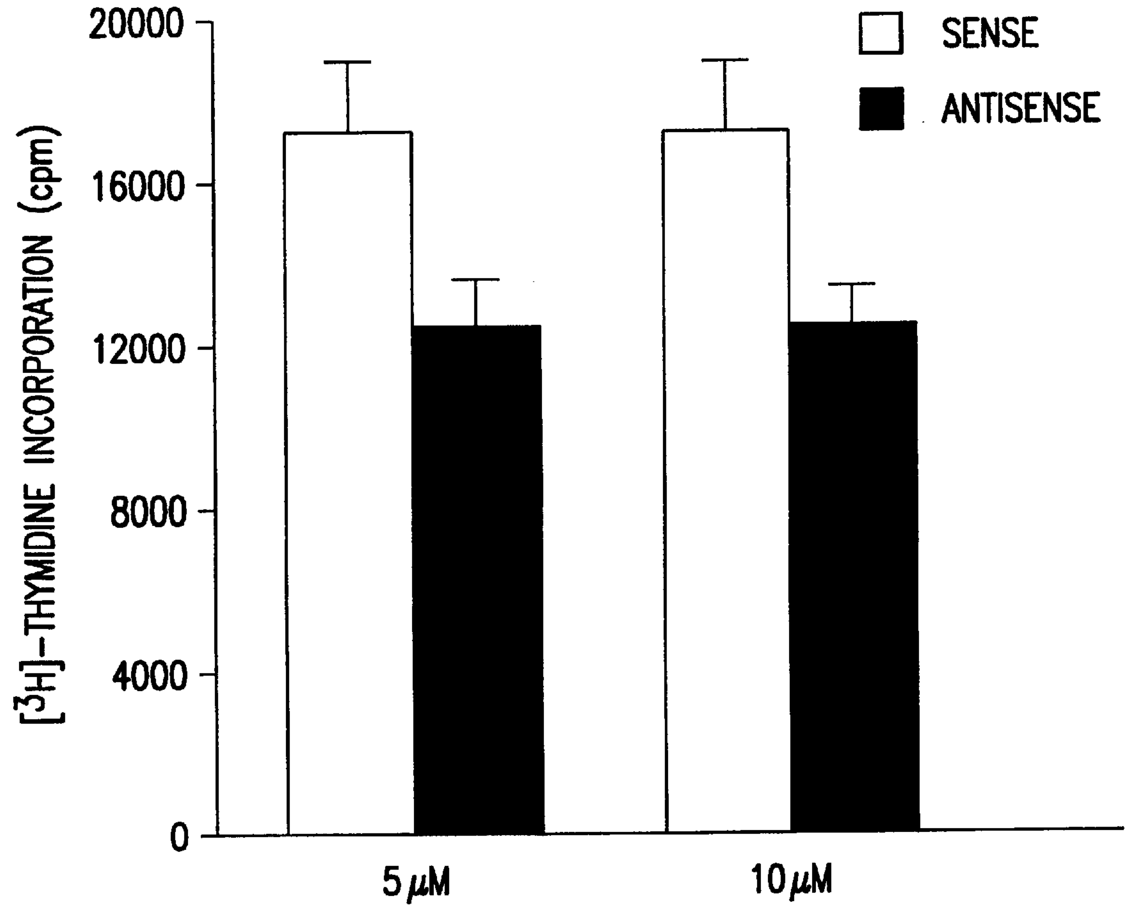
FIG. 5. Depicts a graph which shows the effect of p43 antisense oligodeoxynucleotide on the IL-2 induced DNA synthesis. FWT-2 cells were analyzed for their ability to incorporate $[^3H]$ thymidine in the presence of antisense oligodeoxynucleotide after IL-2 stimulation. The data are represented as the average of triplicate determinations.

The effect of p43 sense and antisense oligomers in $[^3H]$ thymidine incorporation after IL-2 stimulation as a parameter of growth was evaluated as shown in FIG. 5 . The experiments have been repeated at least three times. It is evident that the p43 antisense oligodeoxynucleotide partially inhibits the $[^3H]$ thymidine incorporation (~30%). On the other hand, no effect was observed using sense oligodeoxynucleotides. These results suggest that p43 molecule alters the IL-2 signal partially, but does not inhibit the full scale signal. It remains to evaluate the presence of redundant associated molecules, which can compensate for the absence of p43 in the presence of antisense oligonucleotides.

Example 5

$NAD^+$ Binding Assay

Figure 6:
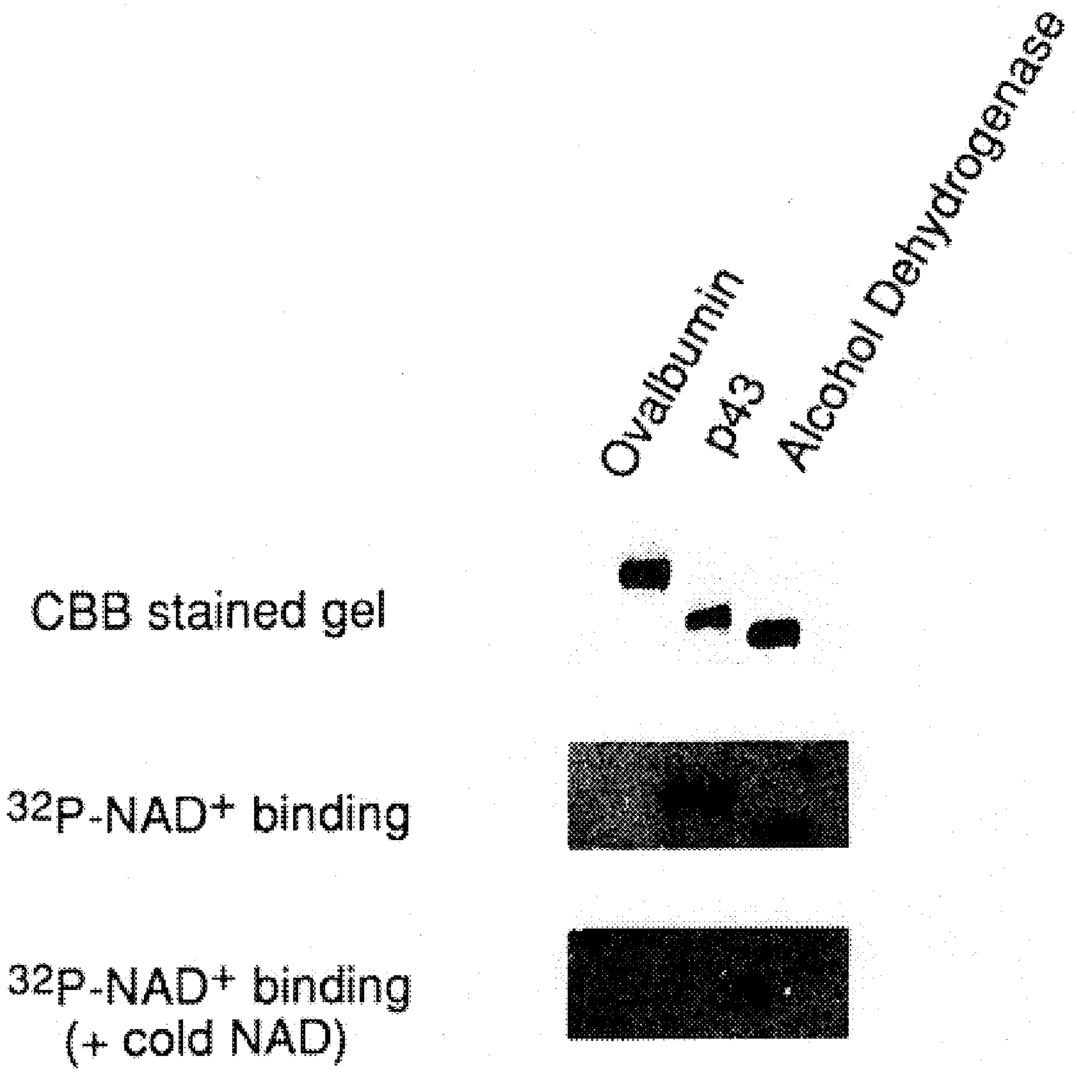
FIG. 6. Depicts a radiogram which shows binding to p43. $[^{32}P]$ $NAD^+$ was incubated with the filter, which was transferred with ovalbumin, the recombinant p43 and alcohol dehydrogenase proteins, in the binding buffer (see Materials and Methods). Then, the filter was washed and exposed.

As mentioned earlier, p43 has partial homology to $NAD^+$ binding proteins, such as alcohol dehydrogenase. To confirm whether p43 can bind $NAD^+$, we performed $NAD^+$ binding assay. We first tested the binding of $NAD^+$to recombinant p43 produced in bacteria. The complete open reading frame of p43 was fused to 6xHis tag sequences, and the resulting chimeric protein was purified from overexpressing bacterial strains by affinity chromatography on Ni-column. For the recombinant *E. coli* expressing p43, the p43 chimeric protein fused to the 6xHis affinity tag was constructed using vector, 6HisT-pET11d, which was kindly obtained from Mr. Hashimoto (Rockefeller University). Plasmid was transformed into *E. coli* strain BL21/pLysS, and recombinant p43 was purified using Ni-column (Invitrogen). Purified p43 and control proteins (ovalbumin and alcohol dehydrogenase) were applied to SDS-PAGE (10–20% gradient gel), and electrophoretically transferred onto PVDF membrane filters. After soaking in the binding buffer [50 mM Tris-HCl pH7.5, 1 mM EDTA, 5 mM $MgCl_2$, 0.3% (v/v) Tween 20] at room temperature for 1 hr, the membrane filters were incubated with $[^{32}P]$ NAD in the binding buffer at 20° C. for 18 hrs. The filters were then washed with the binding buffer three times and exposed to X-ray film. As shown in FIG. 6, we detected the $NAD^+$binding ability of p43. On the other hand, its binding ability could be completely abolished in the presence of deleted excess cold NAD.

Example 6

Immunoprecipitation and Immunoblotting Analysis

For immunoprecipitation and immunoblotting of IL-2R and p43, chimeric genes were constructed as follows: the CD4β, CD4βA, CD4βS, CD4γ and CD4γM1 chimeric receptor expression plasmids, which bear CD4 extracellular and transmembrane domains and the cytoplasmic domains of IL-2R β-chain, IL-2R β-chain lacking the internal "S-region" and the "A-region", IL-2R γ-chain, and the membrane proximal 7 amino acids of the cytoplasmic domain of IL-2R γ-chain, respectively, were constructed as described previously (18). Briefly, the CD4β and CD4γ chimeric receptors are comprised of human CD4 extracellular/transmembrane domains, fused in frame with the cytoplasmic domains of IL-2Rβ and IL-2Rγ chains respectively, using the two pairs of synthesized oligonucleotides. The CD4β and CD4γ cDNAs were inserted into the EcoRI/XbaI cleaved pEF vector (25) (pEF-CD4β and pEF-CD4γ) respectively. To construct the expression vectors (pEF-CD4βA and CD4βS) for the chimeric molecules, CD4βA and CD4βS, the pdKCRA and pdKCRS vectors (8), respectively, were digested with NcoI and BamHI. After digestion, the respective NcoI-BamHI fragments (~0.9Kb) were inserted into the NcoI/BamHI-cleaved pEF-CD4β vector. The LCK-p43 chimeric molecule is comprised of the $p56^{lck}$ N-terminal region (~100 amino acids), mutated in the myristilation site from Gly to Ala, fused in frame with p43 using the PCR fragment of LCK. The LCK-p43 cDNA was inserted into pEF vector (25). The constructs were confirmed by restriction enzyme digestion and DNA sequencing.

The experiments for transient cDNA expression studies in COS cells were performed as described previously (7). The immunoprecipitation using anti-CD4 antibody (OKT4) and immunoblotting analysis using anti $p56^{lck}$ antiserum were also performed as described previously (18).

Example 7

Production of Antibodies

Polyclonal antibodies have been raised against the following synthetic peptides corresponding to different sequence motifs of p43:

SEQ ID NO: 10: CKVVQKPSVRRISTTSPRST (a.a. 23–41)

SEQ ID NO: 11: CYKSGSVEEQLKSLKPFDFI (a.a. 255–273)

SEQ ID NO: 12: CGGSTETWAPDFLKKWSGAT (a.a. 278–296)

The protocol of antigenic conjugate preparation, immunization and antibody titer determination is as follows:

The protocol for the conjugation of sulfhydryl-containing peptides to the carrier protein KLH was utilized. In brief, 1 mg of peptide and keyhole limpet hemocyamine (KLH, cf. 34, vol. I, p. 26) in 500 $\mu$l of PBS were mixed with 500 $\mu$l of complete Freund's adjuvant using Luer-lock connected syringes. After testing the proper mixing of the conjugate components, rabbits were injected subcutaneously in the back of the neck. The animals were boosted with 500 $\mu$g of antigen (conjugate mixed with incomplete Freund's adjuvant), at intervals of two weeks for a period of three months.

The antiserum was periodically tested using an enzyme-linked immunosorbant assay (ELISA), where the peptide KLH conjugate at 1 $\mu$g/$\mu$l was coated into ninety-six well microplates in coating buffer (0.1 M $NaHCO_3$ pH 9.0). After washing the microplate with rinse buffer (PBS, 0.1% Tween 20), different dilutions of the immune sera or control sera were added in a volume of 50–100 $\mu$l to the wells and incubated at room temperature for two hours.

The plates were washed with rinse buffer and 50 $\mu$l of goat anti-rabbit IgG conjugated with alkaline phospatase in PBS and 1% BSA and 0.1% Tween 20 was added to the wells and incubated for two hours at room temperature. The microplate was washed with rinse buffer and 100 $\mu$l of substrate, p-phenyl phosphate disodium in substrate buffer was added to the wells. The microplate was incubated at room temperature for 1–2 hours and the optical density (OD) at 405 nm measured (ref. 620 nm).

The three different anti-peptide antibodies could recognize the peptide conjugate at a dilution of $1/10^4$. The antibody against peptide SEQ ID NO: 11 could also recognize the *E. coli* expressed recombinant human p43.

REFERENCES

1. Bazan, J. F. 1990. Structural design and molecular evolution of a cytokine receptor superfamily. Proc. Natl. Acad. Sci. USA 87:6934–6938.
2. Cosman, D., S. D. Lyman, R. L. Idzerda, M. P. Beckmann, L. S. Park, R. G. Goodwin, and C. J. March. 1990. A new cytokine receptor superfamily. Trends Biochem. Sci. 15:265–269.
3. Doi, T., M. Hatakeyama, S. Minamoto, T. Kono, H. Mori, and T. Taniguchi. 1989. Human interleukin 2 (IL-2) receptor β chain allows transduction of IL-2-induced proliferation signal(s) in a murine cell line. Eur. J. Immunol. 19:2375–2378.
4. Durfee, T., K. Becherer, P.-L. Chen, S.-H. Yeh, Y. Yang, A. E. Kilburn, W.-H. Lee, and S. J. Elledge. 1993. The retinoblastoma protein associates with the protein phophatase type 1 catalytic subunit. Genes Dev. 7:555–569.
5. Greene, W. C. and W. J. Leonard. 1986. The human interleukin-2 receptor. Annu. Rev. Immunol. 4:69–96.
6. Hatakeyama, M., A. Kawahara, H. Mori, H. Shibuya, and T. Taniguchi. 1992. c-fos gene induction by IL-2: identification of the critical cytoplasmic regions within the IL-2 receptor β chain. Proc. Natl. Acad. Sci. USA 89:2022–2026.
7. Hatakeyama, M., T. Kono, N. Kobayashi, A. Kawahara, S. D. Leven, R. M. Parlmutter, and T. Taniguchi. 1991. Interaction of the IL-2 receptor with the src-family kinase $p56^{lck}$: Identification of novel intermolecular association. Science 252:1523–1528.
8. Hatakeyama, M., H. Mori, T. Doi, and T. Taniguchi. 1989. A restricted cytoplasmic region of IL-2 receptor β chain is essential for growth signal transduction but not for ligand binding and internalization. Cell 59:837–845.
9. Hatakeyama, M., M. Tsudo, S. Minamoto, T. Kono, T. Doi, T. Miyata, M. Miyasaka, and T. Taniguchi. 1989. Interleukin-2 receptor P chain gene: Generation of three receptor forms by cloned human α and β chain cDNAs. Science 244:551–556.
10. Johnston, J. A., M. Kawamura, R. A. Kirken, Y.-Q. Chen, T. B. Ortaldo, D. W. McVicar, and J. J. O'Shea. 1994. Phosphorylation and activation of the Jak-3 Janus kinase in response to interleukin-2. Nature 370:151–153.
11. Kawahara, A., Y. Minami, and T. Taniguchi. 1994. Evidence for a critical role for the cytoplasmic region of the interleukin 2 (IL-2) receptor γ chain in IL-2, IL-4 and IL-7 signalling. Mol. Cell. Biol. 14:5433–5440.
12. Kim, H., E. L. Jacobson, and M. K. Jacobson. 1993. Synthesis and degradation of cyclic ADP-ribose by NAD glycohydrolases. Science 261:1330–1333.
13. Kobayashi, N., T. Kono, M. Hatakeyama, Y. Minami, T. Miyazaki, R. M. Perlmutter, and T. Taniguchi. 1993. Functional coupling of the src-family protein tyrosine kinases p59fyn and $p53/56^{lyn}$ with the interleukin 2 receptor: Implications for redundancy and pleiotropism in cytokine signal transduction. Proc. Natl. Acad. Sci. USA 90:4201–4205.
14. Kondo, M., T. Takeshita, M. Higuchi, M. Nakamura, T. Sudo, S. Nishikawa, and K. Sugamura. 1994. Functional participation of the IL-2 receptor γ chain in IL-7 receptor complexes. Science 263:1453–1454.
15. Kondo, M., T. Takeshita, N. Ishii, M. Nakamura, S. Watanabe, K. Arai, and K. Sugamura. 1993. Sharing of the interleukin-2 (IL-2) receptor γ chain between receptors for IL-2 and IL-4. Science 262:1874–1877.
16. Minami, Y., T. Kono, T. Miyazaki, and T. Taniguchi. 1993. The IL-2 receptor complex: Its structure, finction, and target genes. Annu. Rev. Immunol. 11:245–267.
17. Minami, Y., T. Kono, K. Yamada, N. Kobayashi, A. Kawahara, R. M. Perlmutter, and T. Taniguchi. 1993. Association of p56lck with IL-2 receptor β chain is critical for the IL-2-induced activation of $p56^{lck}$. EMBO J. 12:759–768.
18. Minami, Y., Y. Nakagawa, A. Kawahara, T. Miayazaki, K. Sada, H. Yamamura, and T. Taniguchi. 1995. Protein tyrosine kinase Syk is associated with and activated by the IL-2 receptor; possible link with the c-myc induction pathway. Immunity 2(1):89–100.
19. Nakamura, Y., S. M. Russell, S. A. Mess, M. Friedmann, M. Erdos, C. Francois, Y. Jacques, S. Adelstein, and W. J. Leonard. 1994. Heterodimerization of the IL-2 receptor β- and γ-chain cytoplasmic domains is required for signalling. Nature 369:330–333.
20. Nelson, B. H., J. D. Lord, and P. D. Greenberg. 1994. Cytoplasmic domains of the interleukin-2 receptor β and γ chains mediate the signal for T-cell proliferation. Nature 369:333–336.
21. Noguchi, M., Y. Nakamura, S. M. Russell, S. F. Ziegler, M. Tsang, X. Cao, and W. J. Leonard. 1993. Interleukin-2 receptor y chain: a functional component of the interis leukin-7 receptor. Science 262:1877–1880.
22. Noguchi, M., H. Yi, H. M. Rosenblatt, A. H. Filipovich, S. Adelstein, A. S. Modi, O. W. McBride, and W. J. Leonard. 1993. Interleukin-2 receptor γ chain mutation results in X-linked severe combined Immunodeficiency in human. Cell 73:147–157.

23. Russell, S. M., A. D. Keegan, N. Harada, Y. Nakamura, M. Noguchi, P. Leland, M. C. Friedmann, A. Miyajima, R. K. Puri, W. E. Poul, and W. J. Leonard. 1993. Interleukin-2 receptor γ chain: a fimctional component of the interleukin-4 receptor. Science 262:1880–1883.

24. Satoh, T., Y. Minami, T. Kono, K. Yamada, A. Kawahara, T. Taniguchi, and Y. Kaziro. 1992. Interleukin 2-induced activation of ras requires two domains of Interleukin 2 receptor β subunit, the essential region for growth stimulation and lck-binding domain. J. Biol. Chem. 267:25423–25427.

25. Shibuya, H., K. Irie, J. Ninomiyα-Tsuji, M. Goebl, T. Taniguchi, and K. Matsumoto. 1992. New human gene encoding a positive modulator of HIV Tat-mediated transactivation. Nature 357:700–702.

26. Shibuya, H., M. Yoneyama, J. Ninomiyα-Tsuji, K. Matsumoto, and T. Taniguchi. 1992. IL-2 and EGF receptors stimulate the hematopoietic cell cycle via different signaling pathways: Demonstration of a novel role for c-myc. Cell 70:57–67.

27. Smith, K. A. 1988. Interleukin 2: inception, impact and implications. Science 240:1169–1176.

28. Takeshita, T., H. Asao, K. Ohtani, N. Ishii, S. Kumaki, N. Tanaka, H. Munakata, M. Nakamura, and K. Sugamura. 1992. Cloning of the γ chain of the human IL-2 receptor. Science 257:379–382.

29. Taniguchi, T. and Y. Minami. 1993. The IL-2/IL-2 receptor system: A current overview. Cell 73:5–8.

30. Waldmann, T. A. 1989. The multi-subunit interleukin-2 receptor. Annu. Rev. Biochem. 58:875–911.

31. Witthuhn, B. A., O. Silvennoinen, 0. Miura, K. S. Lai, C. Cwik, E. T. Liu, and J. N. Ihle. 1994. Involvement of the Jak3 Janus kinase in signalling by interleukin 2 and 4 in lymphoid and myeloid cells. Nature 370:153–157.

32. Sambrook, J., E. F. Fritsch, and T. Maniatis. 1989. Molecular cloning. A laboratory manual. Second edition. Cold Spring Harbour Laboratory Press.

33. Creighton, T. E. (ed.). 1989. Protein function—a practical approach. IRL press, Oxford.

34. Catty, D. (ed.). 1989. Antibodies—a practical approach. Vols. I and 2. IRL press, Oxford.

35. Wunderlich, D., A. Lee, R. P. Fracasso, D. V. Mierz, R. M. Bayney, T. V. Ramabhadran. 1992. Use of recombinant fusion proteins for generation and rapid characterization of monoclonal antibodies. J. Immunol. Methods 147:1–11.

36. Osol, A. (ed.). 1980. Remington's Pharmaceutical Sciences (16th ed.). Mack, Easton, Pa.

37. Fields, S., O. Song. 1989. A novel genetic system to detect protein-protein interactions. Nature 340: 245–246.

38. Kono T. et al. 1989. Proc. Natl. Acad. Sci. U.S.A. 87: 1806–1810.

What is claimed is:

1. An isolated nucleic acid molecule encoding a polypeptide comprising the amino acid sequence of SEQ ID NO:2 or SEQ ID NO:4.

2. An isolated polypeptide encoded by the nucleic acid molecule of claim 1.

3. An isolated polypeptide, comprising the amino acid sequence of SEQ ID NO: 2 or SEQ ID NO: 4.

4. A vector comprising the isolated nucleic acid molecule of claim 1.

5. The vector of claim 4, said vector being an expression vector.

6. A host cell comprising the vector of claim 5.

7. A method of producing the polypeptide of claim 2, comprising the steps of (a) cultivating a host cell transformed, transduced or transfected with said nucleic acid molecule, under conditions where said polypeptide is expressed by said host cell; and (b) isolating said polypeptide.

8. The method of claim 7, wherein said host cell is an *E. coli* cell.

9. The method of claim 7, wherein said host cell is a mammalian cell.

10. The host cell of claim 9, which is a COS cell.

11. A composition comprising the isolated polypeptide of claim 2 and an acceptable carrier.

12. A composition comprising the isolated nucleic acid molecule of claim 1 and an acceptable carrier.

* * * * *